United States Patent [19]

Bernardin et al.

[11] Patent Number: 5,124,197
[45] Date of Patent: Jun. 23, 1992

[54] INFLATED CELLULOSE FIBER WEB POSSESSING IMPROVED VERTICAL WICKING PROPERTIES

[75] Inventors: Leo J. Bernardin, Appleton; Patti J. Rhode, Rosendale; Catherine J. Heimbach, Stockbridge, all of Wis.

[73] Assignee: Kimberly-Clark Corporation, Neenah, Wis.

[21] Appl. No.: 386,846

[22] Filed: Jul. 28, 1989

[51] Int. Cl.⁵ .................................................. B32B 5/06
[52] U.S. Cl. ........................................ 428/284; 428/224; 428/297; 428/298; 428/393; 428/398; 428/913; 428/288; 604/367; 604/368; 604/374; 604/378
[58] Field of Search ................ 604/367, 368, 374; 428/224, 393, 913, 398, 284, 298, 297, 288

[56] References Cited

U.S. PATENT DOCUMENTS

| | | | |
|---|---|---|---|
| 3,069,311 | 12/1962 | Harpham et al. | 162/146 |
| 3,224,926 | 12/1965 | Bernardin | 162/146 |
| 3,241,553 | 3/1966 | Steiger | 128/156 |
| 3,320,956 | 5/1967 | Steiger | 128/263 |
| 3,339,550 | 9/1967 | Van Haaften | 128/290 |
| 3,423,167 | 1/1969 | Kuzmak | 8/129 |
| 3,589,364 | 6/1971 | Dean et al. | 128/284 |
| 3,626,045 | 12/1971 | Woodings | 264/54 |
| 3,658,613 | 4/1972 | Steiger | 156/153 |
| 3,936,441 | 2/1976 | Holst et al. | 260/231 A |
| 3,971,379 | 7/1976 | Chatterjee | 128/285 |
| 3,993,553 | 11/1976 | Assarsson et al. | 204/159.12 |
| 4,047,531 | 9/1977 | Karami | 128/290 R |
| 4,051,086 | 9/1977 | Reid | 260/17.4 GC |
| 4,062,451 | 12/1977 | Gander | 206/524.2 |
| 4,130,689 | 12/1978 | Costa, Jr. | 428/398 |
| 4,179,416 | 12/1979 | Smith | 260/17.4 CL |
| 4,232,674 | 11/1980 | Melican | 128/287 |
| 4,242,242 | 12/1980 | Allen | 260/17.4 CL |
| 4,307,721 | 12/1981 | Tsuchiya et al. | 128/290 W |
| 4,388,256 | 6/1983 | Ishida et al. | 264/41 |
| 4,391,872 | 7/1983 | Suzuki et al. | 428/224 |
| 4,392,908 | 7/1983 | Dehnel | 427/194 |
| 4,443,492 | 4/1984 | Roller | 427/44 |
| 4,444,830 | 4/1984 | Erickson | 428/246 |
| 4,617,326 | 10/1986 | Björnberg et al. | 523/111 |
| 4,822,453 | 4/1989 | Dean et al. | 162/157.6 |

FOREIGN PATENT DOCUMENTS

| | | |
|---|---|---|
| 0095917 | 12/1983 | European Pat. Off. |
| 0210570 | 2/1987 | European Pat. Off. |
| 0212289 | 3/1987 | European Pat. Off. |
| 0251673 | 1/1988 | European Pat. Off. |
| 0251674 | 1/1988 | European Pat. Off. |
| 0251675 | 1/1988 | European Pat. Off. |
| 0251676 | 1/1988 | European Pat. Off. |
| 0252649 | 1/1988 | European Pat. Off. |
| 0252650 | 1/1988 | European Pat. Off. |
| 865843 | 8/1959 | United Kingdom |
| 1160625 | 4/1967 | United Kingdom |
| 2094637 | 9/1982 | United Kingdom |
| 8503509 | 8/1985 | World Int. Prop. O. |
| 8804704 | 6/1988 | World Int. Prop. O. |

OTHER PUBLICATIONS

"The Absorbency Characteristics of a Range of Fibers Used in Nonwovens" by A. G. Wilkes.
"The Manufacture Properties and Uses of Inflated Viscose Fibres" by A. J. Bartholomew, et al.-Journal of Industrial Fabrics 4, No. 1 (1985).
"The Absorption of Liquids by Compressed Fiber Systems" by Fred Steiger, et al.-Textile Research Journal vol. 42, Aug., 1972.

*Primary Examiner*—James J. Bell
*Attorney, Agent, or Firm*—Thomas J. Mielke

[57] ABSTRACT

An absorbent web formed from inflated cellulose fibers said webs possessing improved vertical wicking properties compared to a similar web of cellulose fibers. The webs have been found to be particularly well suited for use in forming absorbent products such as diapers and the like. In one aspect of the present invention, the inflated cellulose fibers are generally free of a surface finish. In a second aspect the inflated cellulose fibers are crosslinked.

32 Claims, 16 Drawing Sheets

INFLATED CELLULOSE FIBER WEB POSSESSING IMPROVED VERTICAL WICKING PROPERTIES

BACKGROUND OF THE INVENTION

1. Field of the Invention

The present invention relates to the field of absorbent webs. Specifically, the present invention concerns absorbent webs formed from inflated cellulose fibers.

2. Description of the Related Art

Methods of forming tubular filaments of regenerated cellulose material are known. For example, U.S. Pat. No. 3,626,045 issued Dec. 7, 1971 to Woodings describes a process for making tubular rayon filaments. The process described in U.S. Pat. No. 3,626,045 is directed to producing regenerated cellulose filament of which at least ninety (90) percent by number in a cross-section of spun tow have not collapsed to a flattened state.

U.S. Pat. No. 4,130,689 issued Dec. 19, 1978, to Costa, Jr., is directed to the production of high strength hollow rayon fibers. Costa describes a process for producing rayon fibers which are hollow and which do not collapse into a flattened state even after repeated washing and drying cycles.

The formation of carded webs from inflated rayon fibers is described by Bartholomew et al. in "The Manufacture Properties And Uses of Inflated Viscose Fibers", *Journal of Industrial Fabrics*. Vol. 4 No 1:4–17 (1985) and by Wilkes et al. in "The Absorbency Characteristics of a Range of Fibers used in Nonwovens", *Insight* (1985).

None of the above references describe absorbent articles, such as diapers, made from the inflated rayon fibers. Additionally, none of the references is concerned with improving the properties of the filaments such that the filaments are better suited for use in absorbent articles.

U.S. Pat. No. 3,241,553 issued Mar. 22, 1966, to Steiger is directed to a surgical dressing. Specifically, Steiger describes an absorbent dressing formed from crosslinked cellulose fibers. The cellulose fibers employed by Steiger include, in one example, solid-core rayon fibers. Crosslinking of the cellulose fibers is described as improving the fluid absorbing and retention properties of the fibers.

Unfortunately, Steiger neither describes nor suggests an absorbent article formed from inflated rayon fibers or means of treating such fibers to provide them with improved vertical wicking properties.

SUMMARY OF THE PRESENT INVENTION

It is desirable to produce a web of absorbent material which web possesses improved vertical wicking properties. Such a web is well suited to distribute a liquid applied to the web throughout a major portion of the web.

Additionally, it is desirable to provide an incontinence care product such as a diaper which product comprises such an absorbent web. Further, it is desirable to provide an incontinence care product comprising such an absorbent web which absorbent web is in flow (fluid) communication with an amount of a water-swellable polymer. The absorbent web should be capable of transporting a liquid applied to a first location on said web to a second location remote from the first location whereby the liquid transported to the second location is absorbed by the water-swellable polymer.

These and other related goals are achieved by providing an absorbent web of material which material comprises inflated cellulose fibers formed from regenerated cellulose which fibers are generally free of a surface finish. Such an absorbent web has been found to possess improved vertical wicking properties compared to a similar web formed from inflated regenerated cellulose fibers which comprise a surface finish. When such a web is incorporated into an incontinence care product, the incontinence care product is capable of quickly distributing a liquid applied to a first location on the web to locations remote from the first location.

In a second aspect, the present invention concerns an absorbent web of material, which material comprises inflated cellulose fibers formed from regenerated cellulose which inflated cellulose fibers have been crosslinked. Such a web has been found to possess improved vertical wicking properties compared to a web of inflated cellulose fibers formed from regenerated cellulose which fibers have not been crosslinked. Again, when such an absorbent web forms part of an incontinence care product, such as a diaper, the incontinence care product exhibits a greater ability to distribute a fluid applied to a first location on the web to a second location remote from the first location. In this manner, a greater portion of the absorbent web is utilized to absorb the liquid.

DETAILED DESCRIPTION OF THE PREFERRED EMBODIMENT

Figure 1:
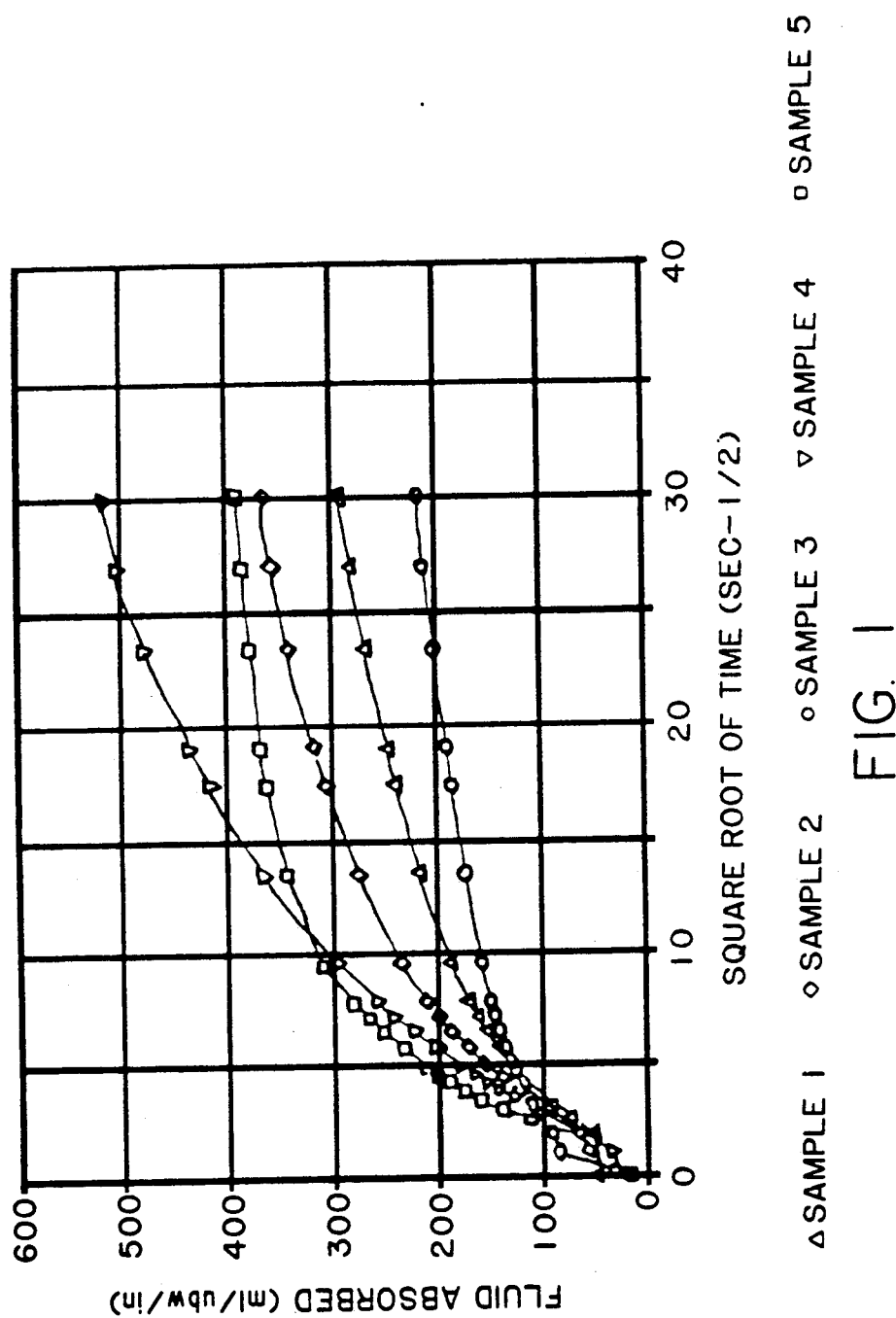
FIG. 1 is a graphical representation of the vertical wicking data for the material in Table 1.

The present invention relates generally to an absorbent web of a material. The material comprises inflated cellulose fibers which fibers are formed from regenerated cellulose (rayon). The absorbent webs of the present invention possess improved vertical wicking properties when compared to a similar web as hereinafter defined.

As used herein, the phrase "inflated cellulose fiber" refers to a fiber having an outer side wall which defines an interior lumen. The interior lumen defined by the outer side wall of the fibers need not be continuous over the length of the fiber.

As used herein, the phrase "vertical wicking properties" refers to the properties of the web including, but not limited to, the vertical wicking rate (amount of vertically wicked fluid per unit of time), the vertical wicking capacity (amount of liquid vertically wicked in a given period of time e.g., 15 minutes), the vertical fluid distribution (grams of fluid per gram of fiber vertically wicked to a given distance from the point of contact in a given period of time e.g., 30 minutes), and the like. The specific parameters of the given vertical wicking properties will be discussed in greater detail in connection with the examples below.

As used herein the phrase "similar web" refers to a web having the same density, fiber size, basis weight, formation process, and the like. That is the physical characteristics of webs to be compared are substantially identical except for the specified difference, e.g., having a surface finish, or being non-crosslinked.

Methods of forming inflated cellulose fibers from a regenerated cellulose material are known to those skilled in the art. As a general rule, such methods employ incorporating a blowing agent-type material into a regenerated cellulose solution which solution is then formed into fiber through an extrusion process. The solution is, for example, extruded into an environment which causes the blowing agent-type material present in the regenerated cellulose solution to generate a gas. The gas thus generated forms the interior lumen of the inflated cellulose fibers.

One exemplary method for forming the inflated cellulose fibers suitable for use in the present invention is set forth in U.S. Pat. No. 3,626,045 issued Dec. 7, 1971, to Woodings which is incorporated herein by reference. Other suitable methods of formation are discussed generally in "The Manufacture Properties And Uses of Inflated Viscose Fibers" *Journal of Industrial Fabrics* Vol. 4 No. 1 (1985) by Bartholomew, A. J. et al., which is similarly incorporated herein by reference. Additionally, it is noted that certain natural fibers similarly possess interior lumens. Exemplary of such natural fibers are certain wood fibers, cotton linters, and cotton staple.

The inflated cellulose fibers suitable for use in the present invention generally have a fineness of from about 1 to about 8 denier, preferably from about 1.5 to about 3.0 denier. The fibers generally have a length of at least about 2.0 millimeters. One example of a commercially available inflated cellulose fiber formed from a regenerated cellulose material and suitable for use in the present invention is available from Courtaulds Limited, of London, England, under the trade designation Viloft TM or Courcel TM.

Inflated rayon fibers are known to produce yarns which have an increased bulk compared to yarns made from solid rayon fibers. Additionally, fabrics formed from the yarns of inflated rayon fibers are stated to have a hand similar to cotton and a greater absorbency.

In a first aspect, the inventors have found that a nonwoven web formed from inflated rayon fibers which fibers have been treated to be generally free of a surface finish, possesses improved vertical wicking properties compared to a similar nonwoven web having the same physical characteristics e.g. density, fiber length, fiber fineness, unit basis weight, etc. but formed from inflated rayon fibers which possess a surface finish.

In a second aspect, the present invention concerns the discovery that crosslinked inflated cellulose fibers demonstrate improved vertical wicking properties when compared to absorbent webs of non-crosslinked inflated cellulose fibers. Accordingly, in this second aspect, the present invention is directed to an absorbent web formed from a material comprising crosslinked inflated cellulose fibers. In a preferred embodiment of this aspect of the present invention, the inflated cellulose fibers are formed from a regenerated cellulose material.

Absorbent webs formed from crosslinked inflated cellulose fibers possess improved vertical wicking properties when compared to webs of non-crosslinked inflated cellulose fibers. In contradistinction, crosslinking noninflated solid core rayon fibers has not been found to produce a web possessing improved vertical wicking properties when compared to a web of non-crosslinked noninflated solid core cellulose fibers. That is, crosslinking has been found beneficial when used in connection with inflated rayon fibers while it has not proven beneficial, from a vertical wicking standpoint, in connection with noninflated rayon fibers.

As a general rule, the vertical wicking properties of a web according to the present invention will be considered to be improved when the web exhibits at least about a 20 percent increase in initial vertical wicking rate, vertical wicking capacity (at 15 or 30 minutes), or vertical fluid distribution (at a distance between nine (9) and eighteen (18) centimeters) when compared to the defined similar web. Preferably, the webs according to the present invention exhibit one or more vertical wicking property which is at least about 40 percent greater than that property exhibited by the similar web to which it is compared. Additionally, it is most preferred that the webs according to the present invention demonstrate at least about a 20 percent, preferably at least about a 40 percent improvement in at least two (2) vertical wicking properties when compared to the defined similar web.

Methods of forming absorbent webs from cellulose fibers are known to those skilled in the art. For example, the webs may be formed by air laying, wet laying, carding, or the like. Since the various ways of forming the web will often affect the pore structure of the web, webs according to the present invention which are formed by different processes, may demonstrate different vertical wicking properties. Nonetheless, the vertical wicking properties of webs according to the present invention are improved when compared to the similar webs.

As a general rule, the webs according to the present invention will have a density of from about 0.05 to about 0.4 grams per cubic centimeter. For non-crosslinked webs according to the present invention, the preferred density is within the range of from about 0.1 to about 0.2 grams per cubic centimeter. For crosslinked webs according to the present invention, the preferred density is within the range of from about 0.07 to about 0.2 grams per cubic centimeter. The basis weight of the webs according to the present invention is generally within the range of from about 100 to about 2000 grams per square meter, preferably from about 200 to about 1000 grams per square meter.

Fibers formed from regenerated cellulose materials generally have a chemical surface treatment of a surfactant and/or lubricant present on their outer surface. These surface treatments are present on the regenerated cellulose fibers in order to permit fabrication of the fibers into useful products. Specifically, carding, spinning, weaving or other means of forming such fibers into useful products is generally not possible unless the fibers have a surface treatment as described above.

Applicants have discovered that the presence of such surface treatments has an undesirable effect on the vertical wicking properties of absorbent webs formed from such fibers. This fact has not previously been described. Accordingly, it is often desirable to remove these chemical surface treatments from the exterior surface of the fibers after formation of the webs, in order to obtain the improved wicking properties of the webs of the present invention.

These chemical compounds are suitably removed by solvent extraction or scouring agents through a scouring process. For example, the chemical compounds may generally be removed with methanol through a soxhlet extraction process, or with trisodium phosphate in a hot aqueous scouring. The exact method of removing the surface treatment will depend on the chemical nature of the surface treatment. Suitable means for removal can be easily determined by one skilled in the art. It is desirable to employ a removal means which does not deleteriously affect the fibers themselves.

Methods of crosslinking solid core cellulose fibers are known to those skilled in the art. Methods of crosslinking such solid core cellulose fibers are suitably employed to crosslink inflated cellulose fibers. As a general rule, the webs of cellulose fibers may be crosslinked through either a dry crosslinking process or a wet crosslinking process.

Both wet and dry crosslinking processes involved crosslinking agents which are capable of combining with at least two (2) hydroxyl groups in a cellulose molecule or in adjacent cellulose molecules. The crosslinking agents must be at least bifunctional with respect to cellulose so that they may react with at least two hydroxyl groups. Exemplary of suitable crosslinking agents are formaldehyde, 1,3-dichloro-2-propanol, N,N'-methylenebisacrylamide, glyoxal, dicarboxylic acids, divinyl compounds, diisocyanates, diepoxides, other dihalogen-containing compounds, halohydrins, and the like.

As used herein, the term dry crosslinking refers to a crosslinking process where crosslinking occurs while the cellulose fibers are in a generally nonswollen (dry) form. The term wet crossliking refers to a crosslinking process wherein the cellulose fibers are in a swollen state. Again, these processes are known to those skilled in the art and need not be detailed here.

It has been observed that photomicrographs taken of cross-sections of the webs according to the present invention reveal that a majority of the inflated cellulose fibers present in the webs have collapsed. That is, the fibers have flattened to form structures having an interior lumen which is generally elliptical. Thus, rather than having a structure similar to a drinking straw, wherein the interior lumen is generally circular, the inflated rayon fibers of the webs of the present invention define a generally elliptical lumen such as that demonstrated by pinching opposite side walls of a drinking straw together.

It is hypothesized that this partial collapse may be caused at least in part, by external forces, such as drying and densification encountered during formation of the webs. It is further hypothesized that this ability of the inflated rayon fibers to at least partially collapse leads to the improved vertical wicking properties demonstrated by the webs according to the present invention. Specifically, it is believed that when the inflated fibers are in a partially collapsed state (as they are in a densified web), they are more readily able to develop and maintain a fine pore structure which is believed to be necessary for improved vertical wicking properties. It is to be understood that a liquid being vertically wicked through the webs of the present invention is not generally being wicked through the lumens of the inflated cellulose fibers, as they are not believed to be continuous but are interrupted by membranes. That is, the liquid does not travel as though being drawn up in a drinking straw. Instead, the liquid travels through the pore structure formed by the exterior of the fibers that are adjacent one another in the web.

Solid core rayon fibers do not have the ability to collapse to form the ribbon-like fibers formed when the inflated fibers collapse. Thus, webs formed from solid rayon fibers are not believed to be able to form the same capillary pore structures as the webs according to the present invention. As a result, webs formed from solid core rayon fibers do not possess the same vertical wicking properties of webs according to the present invention. Accordingly, it is desirable that the inflated cellulose fibers employed in forming the webs of the present invention be able to at least partially collapse to form ribbon-like fibers.

The absorbent webs according to the present invention are suitable for use in forming absorbent products such as incontinence products, dressings, feminine pads, and the like. In one embodiment of the present invention the absorbent webs according to the present invention are suitably incorporated into a diaper structure.

Diapers generally comprise an outer layer formed from a generally liquid-impervious material; an absorbent web, such as the webs according to the present invention, adjacent to said outer layer; and a body-liner layer adjacent to the web of absorbent material which body liner is adapted to contact the skin of the wearer. In use, a body fluid such as urine insults the body liner, passes through said body liner and is absorbed into the web of absorbent material. The outer layer prevents the absorbed liquid from passing externally of the diaper structure. Diapers and similar products are generally described in U.S. Pat. Nos. 4,710,187 issued Dec. 1, 1987, to Boland et al.; 4,762,521 issued Aug. 9, 1988, to Roessler et al.; 4,770,656 issued Sep. 13, 1988, to Proxmire et al.; and 4,798,603 issued Jan. 17, 1989 to Meyer et al., which references are incorporated herein by reference.

In use, a body fluid, such as urine, generally insults the diaper at a specific, relatively localized area of the diaper structure. It is important that the absorbent web present in the diaper be able to disperse the fluid applied to the diaper to areas remote from the location at which the fluid is initially applied. It is for this reason that it is desirable to produce an absorbent web having improved vertical wicking properties (ability to transfer fluid in the X-Y plane of the web against the force of gravity) such that when it is necessary for liquid applied to the web to be distributed in a vertical direction, the web is capable of so doing.

In order to increase the absorbent capacity of an absorbent web present in a diaper structure it is known to incorporate into the diaper, in flow communication with the absorbent web, an amount of water-swellable polymeric material. The water-swellable polymeric material functions to absorb a liquid supplied thereto. However, if, as is often the case, the water-swellable polymeric material is located in a position remote from the location to which a body fluid is applied to the web, the water-swellable material cannot absorb the fluid unless the fluid is transported from the location of application to said water-swellable polymeric material. Thus, it is again important that the absorbent web be able to transport fluid from one location on the web to another location on the web. The improved vertical wicking properties of the webs according to the present invention allows fluid applied to the diaper in the crotch area to be vertically wicked to a remote location (such as an area near the waistband of the diaper) which area may have present therein or in flow (fluid) communication therewith, water-swellable polymeric materials. Water-swellable polymeric materials are considered to be in flow (fluid) communication with the webs of the present invention when a liquid present in the webs of the present invention can flow into contact with the water-swellable polymeric materials. For example, the water-swellable polymeric material may be present within and be carried by the webs of the present invention or the polymeric material may be present in a structure (such as a fibrous web) separate from the webs of the present invention but in flow communication therewith.

The present invention can best be understood by reference to the following examples (including comparative examples) which examples are not intended to limit, in any way, the scope of the invention as set forth in the claims.

EXAMPLES

In all of the following examples, the following test procedure is used in determining the vertical wicking properties of the absorbent webs described below. A test sample three (3) inches wide and fifteen (15) inches long is cut from the absorbent web to be tested. The test sample is mounted on a Lucite[2] plate that is ⅜ inch thick, five (5) inches wide and nine and one-half (9.5) inches long. The test sample is symmetrically wrapped on the plate such that it is laid against one longitudinal surface, bent around one edge of the plate, and laid against the opposite longitudinal surface of the plate. In this manner, approximately one-half the length of the test sample is located against one longitudinal surface of the plate with the other half of the test sample being located against the opposite longitudinal surface of the test plate. The test sample is totally supported on its outer surface against the test plate by a 10 mesh nylon screen. The opposite longitudinal ends of the sample are fastened to the Lucite[2] plate by a clamp or similar means which holds the screen and test sample against the plate near the top of the sample.

The plate is suspended vertically over a fluid bath contained in a tray with the longitudinal dimension of the test sample perpendicular to the fluid surface. The fluid is then brought into contact with the test sample by immersing the lower edge of the plate in the fluid so that the U-shaped test sample covering the edge of the Lucite[2] plate is slightly immersed. The amount of fluid absorbed as a function of time is recorded at several time intervals for the 30-minute duration of the test. The amount absorbed is calculated as milliliters per unit basis weight (1 gram per square centimeter) per unit width (1 inch). The tests were replicated six (6) times and the results reported are averages of these six (6) measurements. The vertical wicking capacity is defined as the amount absorbed in the defined units at the end of fifteen (15) minutes and thirty (30) minutes. The reported vertical wicking rate is that measured from the plot of the amount of liquid absorbed per unit basis weight per unit width versus the square root of time (in seconds) over the time interval of ten to thirty seconds[178]. Initial vertical wicking rate refers to the average rate for the time interval of 3–21 seconds.

The fluid distribution data is determined in the following manner. The test sample is removed from the plate at the end of thirty (30) minutes and laid horizontally on a three (3) inch by fifteen (15) inch cutting die which is segmented into nine (9) zones of about 1.7 inches each. The cutting die includes cutting edges across the die width and around the outer perimeter. Several quick blows with a mallet divide the 3-inch wide absorbent strip along the longitudinal axis into nine (9) segments. The segments are weighed, oven dried, and reweighed and the fluid pick-up determined on a gram of fluid per gram of fiber basis (corrected for deposited solids from the fluid).

The fluid employed in the test is a synthetic urine produced as follows. To 900 milliliters of distilled water are added, in the following order, 0.31 grams of monobasic calcium phosphate monohydrate ($CaH_4(PO_4)_2 \cdot H_2O$), 0.68 grams monobasic potassium phosphate ($KH_2PO_4$), 0.48 grams magnesium sulfate heptahydrate ($MgSO_4 \cdot 7H_2O$), 1.33 grams potassium sulfate ($K_2SO_4$), 1.24 grams tribasic sodium phosphate dodecahydrate ($Na_3PO_4 \cdot 12H_2O$), 4.4 grams sodium chloride (NaCl), 3.16 grams potassium chloride (KCl), 0.4 grams sodium azide ($NaN_3$), 8.56 grams urea ($CO(NH_2)_2$), and 0.1 grams Pluronic 10R8 (a nonionic surfactant commercially available from BASF-Wyandotte Corporation). Each of the components is added to the 900 milliliters of distilled water in the order given with each component being dissolved before the next component is added. The resulting solution is then diluted to one liter.

EXAMPLE 1

The following test samples are prepared for determination of vertical wicking properties.

Sample 1

Commercially available solid core rayon fibers are provided in continuous filament tow form. The fibers have a denier of 1.5 and are commercially available as rayon tow from Courtaulds, North America, Inc. The rayon fibers are scoured to remove surface treatments. Trisodium phosphate (TSP) plus Triton X-100 (a commercially available nonionic nonylphenyl surfactant obtainable from the Rohm and Haas Company, Philadelphia, Pa.) is employed as the scouring agent and the scouring is accomplished by steeping 30 grams of the tow in 1200 milliliters of an aqueous solution containing 0.3 grams TSP and 0.3 grams Triton X-100, at 72° C. for about 20 minutes. The tow is recovered by filtration, washed with distilled water and air dried. The scoured rayon fibers are then combed out into a generally uniform web and densified in a press (commercially available from Dake, Grand Haven, Mich. under the trade designation "Dake Laboratory Press", Model No. 44-148). The webs are densified to a density of about 0.12 grams per cubic centimeter.

Sample 2

Commercially available solid core rayon fibers in continuous filament tow form are provided. The fibers are available from American Enka as regular rayon tow and have a denier of about 1.5. The fibers are subjected to a scouring process with TSP/Triton X-100 to remove surface treatments from the fibers. The scouring process is the same as that process employed and described in connection with the preparation of Sample 1. The scoured fibers are then combed out into a generally uniform web and densified in a press (Dake). The webs so formed have a density of about 0.1 grams per cubic centimeter.

Sample 3

The commercially available rayon fibers in continuous filament tow form employed in the formation of Sample 2 are similarly employed in preparing this sample. However, prior to formation of the test web, the rayon fibers are not subjected to a scouring process. The unscoured rayon fibers are again formed into a web by densification in a (Dake). The test web has a density of about 0.13 grams per cubic centimeter.

Sample 4

Inflated rayon fibers in continuous filament tow form are provided. The inflated fibers are available from Courtaulds Limited, London, England. The inflated rayon fibers have a denier of about 1.5. The inflated rayon fibers are subjected to a scouring process employing TSP/Triton X-100 as the scouring agent to remove surface treatments. The scouring process is performed as set forth above in connection with Sample 1. The scoured inflated rayon fiber is then formed into a web by densifying an amount of the hollow rayon fibers in a press (Dake). The webs so formed have a density of about 0.13 grams per cubic centimeter.

Sample 5

An amount of bleached southern kraft pulp (75 percent softwood and 25 percent hardwood) is provided. The pulp is converted into fluff in a hammermill. The fluff thus formed is converted into a web by air-laying and subsequent densification in a press (Dake). The web so formed has a density of about 0.11 grams per cubic centimeter.

The vertical wicking properties of Samples 1 through 5 are then determined in accordance with the process set forth above. The results of the vertical wicking property determination are set forth in Table 1.

TABLE 1

| Sample No. | Web Density (g/cc) | Initial Vertical Wicking Rate | Vertical Wicking Capacity, 15 Minutes | Fluid Distribution | | | | |
|---|---|---|---|---|---|---|---|---|
| | | | | 0[1] | 4.5 | 9 | 13.5 | 18 |
| 1* | 0.12 | 27 | 294 | 4.5 | 4.4 | 3.7 | 2.4 | 1.7 |
| 2* | 0.10 | 28 | 365 | 5.4 | 5.0 | 4.2 | 3.2 | 2.6 |
| 3* | 0.13 | 13 | 219 | 5.2 | 4.0 | 1.9 | 0.5 | 0.1 |
| 4 | 0.13 | 39 | 513 | 7.3 | 6.7 | 5.5 | 4.7 | 4.0 |
| 5* | 0.11 | 50 | 390 | 9.1 | 9.3 | 6.2 | 1.8 | 0.3 |

*Not an example of the present invention
[1]Height in centimeters.

Figure 2:
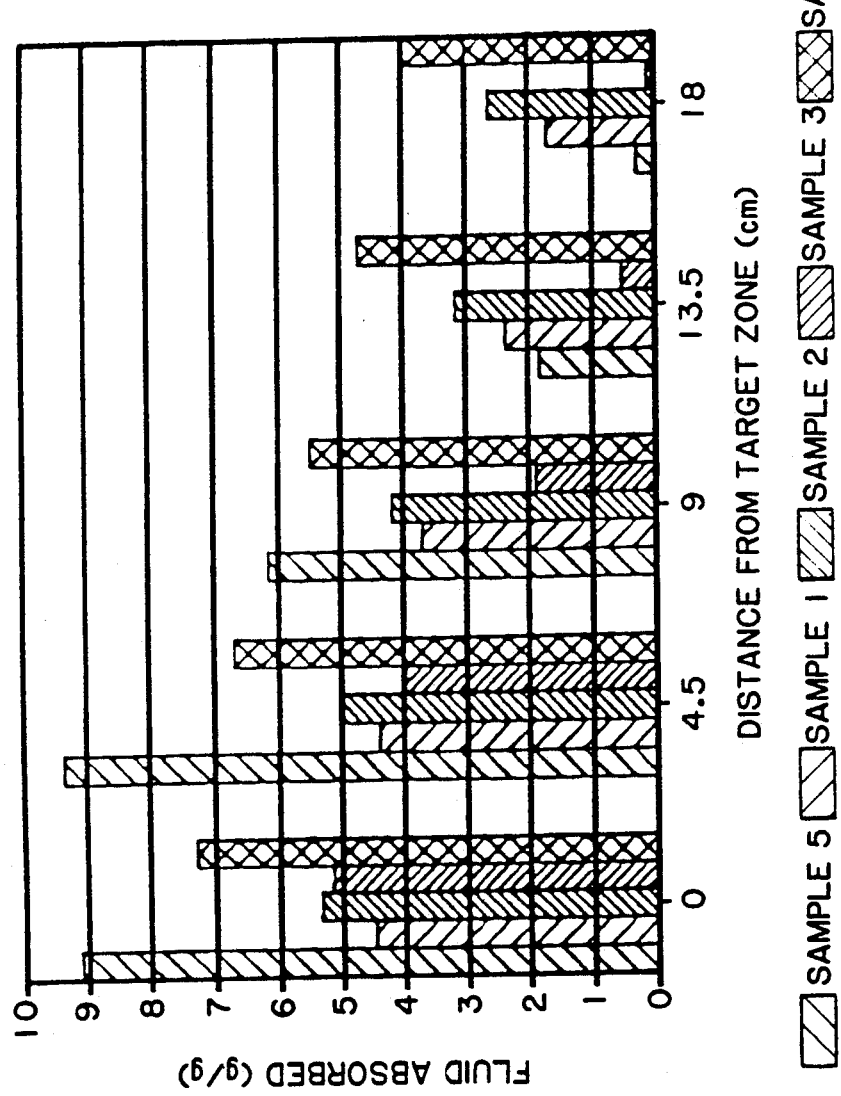
FIG. 2 is a graphical representation of the fluid distribution data set forth in Table 1.

FIG. 1 graphically illustrates the results of the vertical wicking rate set forth in Table 1. FIG. 2 is a bar graph graphically illustrating the fluid distribution data set forth in Table 1.

As can be seen from reference to FIG. 1, the inflated rayon fibers produce a web having an improved vertical wicking rate compared to the solid core rayon fiber webs or the southern kraft pulp fluff web at times greater than about 11 sec[1]. Additionally, by reference to FIG. 2, it is seen that while the fluid distribution for the southern kraft pulp fluff is greatest at 0 to 9 centimeters, the scoured inflated rayon fiber web possesses a fluid distribution value greater than any of the solid core rayon fibers tested. At distances greater than about 9 centimeters the scoured inflated rayon fiber web has a greater fluid distribution than either the wood pulp fluff or the solid core rayon webs.

As discussed above, the ability of an absorbent web to vertically wick fluid to areas remote from the point of liquid application is desirable when the web is intended for use in products such as diapers. It is seen that the scoured inflated rayon fibers produce a web which is superior in both vertical wicking rate and fluid distribution ability. Additionally, it is seen that the scoured inflated rayon web has a vertical wicking capacity of 513 milliliters per unit basis weight per inch compared to the two solid core scoured rayon fiber webs which possess vertical wicking capacities of 365 and 294 milliliters per unit basis weight per inch, respectively. Thus the scoured inflated rayon web demonstrates a 40 percent increase and a 74 percent increase, respectively, compared to the solid core structures.

EXAMPLE 2

Sample 1

Inflated rayon fibers having a denier of 1.5 and commercially available from Courtaulds North America, Inc. under the trade designation Courcel™, are provided. The fibers are formed into carded webs 2 inches wide. The webs are then subjected to soxhlet extraction to remove the surface treatment (sodium oleate and oleic acid). The extraction is performed by placing about four feet of the carded web into each Soxhlet and running the extraction for five hours using methanol as the solvent with about 4 solvent exchanges per hour. The webs are then air dried to remove the solvent. The web is found to have a basis weight of 146 grams per square meter. The webs are then densified in a press (Dake) to a density of 0.15 grams per cubic centimeter.

Sample 1

An amount of the inflated rayon fiber continuous filament tow from Example 1 is provided. The tow is extracted using methanol as the scouring agent in the process set forth in Example 2. Inflated rayon fiber tow is converted into a web by combing and densifying in a press (Dake). The web so formed has a density of about 0.15 grams per cubic centimeter. The measured average fiber angle from the machine direction axis for the tow fiber is 9°.

Sample 2

A portion of the extracted inflated rayon tow of sample 1 is converted into one centimeter staple cut from the tow. The one centimeter staple material so prepared is used to form a random air laid web which is then densified in a press (Dake) to a density of about 0.15 grams per cubic centimeter. The measured average fiber angle from the machine direction axis for the random air laid web is 47°.

Samples 3 and 4

An amount of unscoured inflated rayon fiber tow of Example 1 is obtained as 1-9/16 inch staple under the trade designation Viloft ®. The 1 9/16 inch staple is then used to form random and oriented carded webs. The carded webs are subjected to an extraction process after carding. The solvent employed is methanol and the extraction is accomplished by Soxlet extraction, as described generally in Example 2.

The random carded web (Sample 3) has a measured average fiber angle from the machine direction axis of 38°. The oriented carded web (Sample 4) has a measured average fiber angle from the machine direction axis of 30.5°.

Sample 2

A control sample is provided having a basis weight of 132 grams per square meter which control sample is identical to sample 1 except that it is not subjected to an extraction process and thus retains its surface treatment. The control sample is densified in a press (Dake) to a density of 0.15 grams per cubic centimeter.

Sample 3

A super inflated rayon fiber commercially available from Courtaulds, North America, Inc. under the trade designation SI TM rayon is provided. The super inflated rayon is in the form of 1-9/16 inch staple, has a denier of about 3 and has a surface treatment known as a Leomin finish (polyglycol stearate) present on its exterior surface. The fibers are formed into a carded web having a basis weight of about 55 grams per square meter. Samples are prepared by forming a 5 ply sheet of the carded material and cutting the sheet into 4 × 16 inch test samples. The test samples are then subjected to a solvent extraction process as set forth in connection with Sample 1 using methanol as the solvent. The test samples are then air dried and densified in a press (Dake) to a density of about 0.15 grams per cubic centimeter.

Sample 4

A control sample is provided. The control sample is identical to sample 3 except that it is not subjected to a solvent extraction process and thus retains its surface treatment. The control sample is densified in a press (Dake) to a density of about 0.15 grams per cubic centimeter.

Samples 1–4 are then subjected to vertical wicking property determinations. The results of these determinations are set forth in Table 2.

TABLE 2

| Sample No. | Vertical Wicking Rate Initial | Vertical Wicking Capacity | | Fluid Distribution | | | | |
| --- | --- | --- | --- | --- | --- | --- | --- | --- |
| | | 15 Minutes | 30 Minutes | 0[1] | 4.5 | 9 | 13.5 | 18 |
| 1 | 60 | 748 | 759 | 10.4 | 10.7 | 9.4 | 7.9 | 6.0 |
| 2* | 54 | 495 | 534 | 10.5 | 11.6 | 7.6 | 1.0 | 0.2 |
| 3 | 68 | 810 | 846 | 10.7 | 12.6 | 11.9 | 8.5 | 5.0 |
| 4* | 52 | 481 | 509 | 12.1 | 14.1 | 6.4 | 0.5 | 0.1 |

*Not an example of the present invention
[1]Height in centimeters

As can be seen from reference to Table 2, removal of the surface finish on the rayon webs has a significant effect on the vertical wicking properties of the webs.

Figure 3:
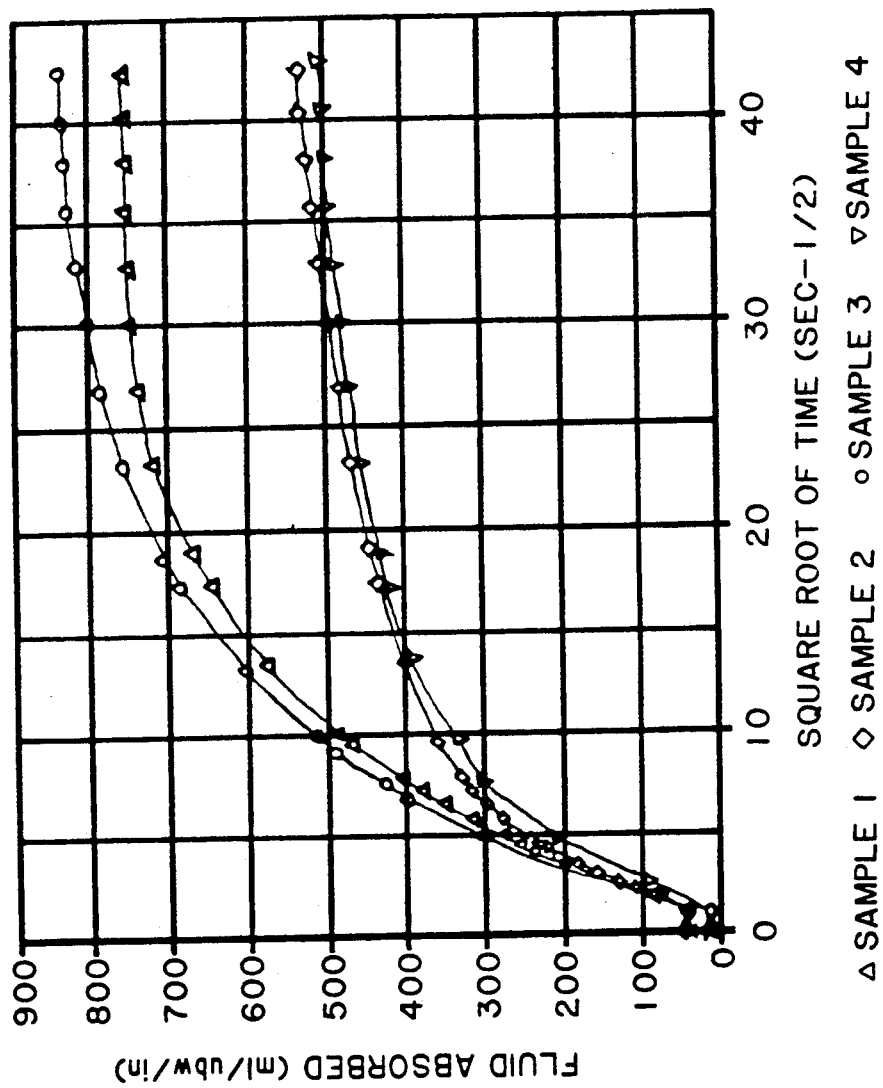
FIG. 3 is a graphical representation of the vertical wicking data for the materials in Table 2.
Figure 4:
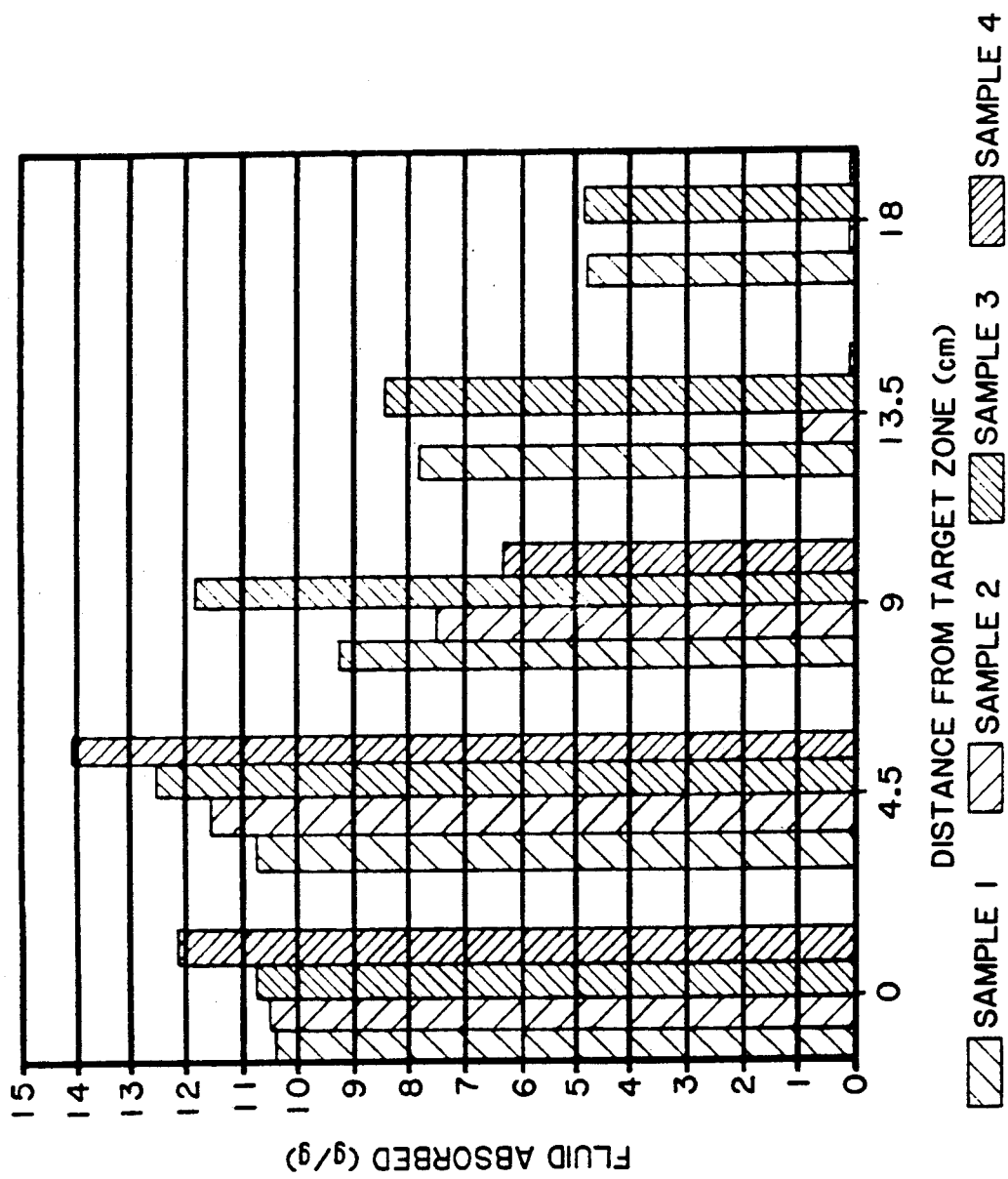
FIG. 4 is a graphical representation of the fluid distribution data set forth in Table 2.

FIGS. 3 and 4 are graphic representations of the data set forth in Table 2. Review of FIGS. 3 and 4 again reveals the improvement achievable in vertical wicking properties in webs according to the present invention.

EXAMPLE 3

Inflated rayon fibers are formed into webs in a variety of manners to test the effect of web formation on vertical wicking properties.

Sample 5

For comparison, an air-laid web is prepared from the southern kraft pulp fluff (CR-54) employed in Example 1. The fluff web is densified to a density of about 0.15 grams per cubic centimeter.

The test samples thus prepared are subjected to vertical wicking property testing. The results of this testing are set forth in Table 3.

TABLE 3

| Sample No. | Vertical Wicking Rate, Initial | Vertical Wicking Capacity, 15 min. | Fluid Distribution (q/q) | | | | |
| --- | --- | --- | --- | --- | --- | --- | --- |
| | | | 0[1] | 4.5 | 9 | 13.5 | 18 |
| 1 | 21 | 500 | 7.2 | 7.0 | 6.2 | 4.7 | 4.1 |
| 2 | 50 | 660 | 10.0 | 11.6 | 10.0 | 4.6 | 1.6 |
| 3 | 70 | 685 | 11.1 | 12.5 | 10.9 | 5.3 | 1.3 |
| 4 | 70 | 760 | 10.3 | 10.8 | 9.4 | 8.0 | 6.0 |
| 5* | 50 | 435 | 8.2 | 9.1 | 7.1 | 2.0 | 0.2 |

*Not an example of the present invention
[1]Height in centimeters

Figure 5:
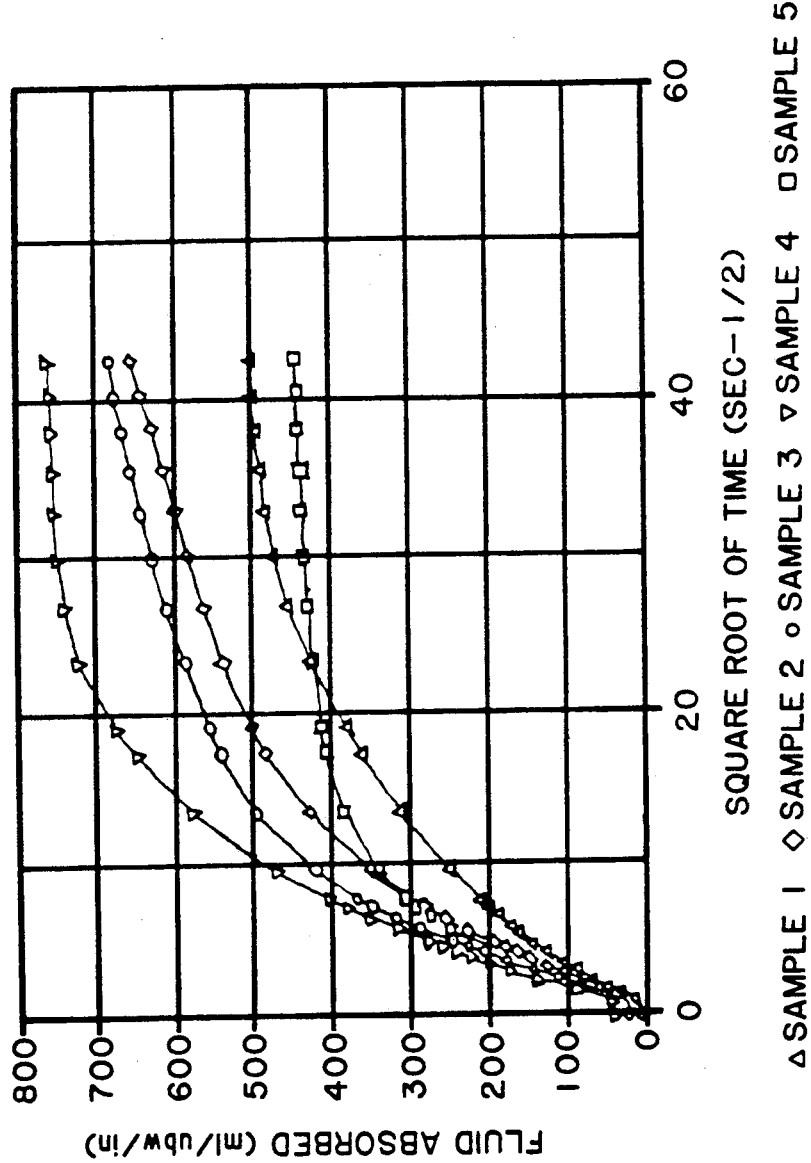
FIG. 5 is a graphical representation of the vertical wicking data for the materials in Table 3.

FIG. 5 is a graphic representation of the results of the vertical wicking rate test data set forth in Table 3. As can be seen from reference to FIG. 5, the oriented carded web has the highest vertical wicking rates at times greater than about 10 seconds[1]. The oriented carded web, random carded web, and air laid web all possess vertical wicking rates superior to the tow web. Clearly, all of the inflated rayon fiber webs possess vertical wicking rates generally superior to the wood pulp fluff at time periods greater than about 25 seconds[1] (625 seconds).

Figure 6:
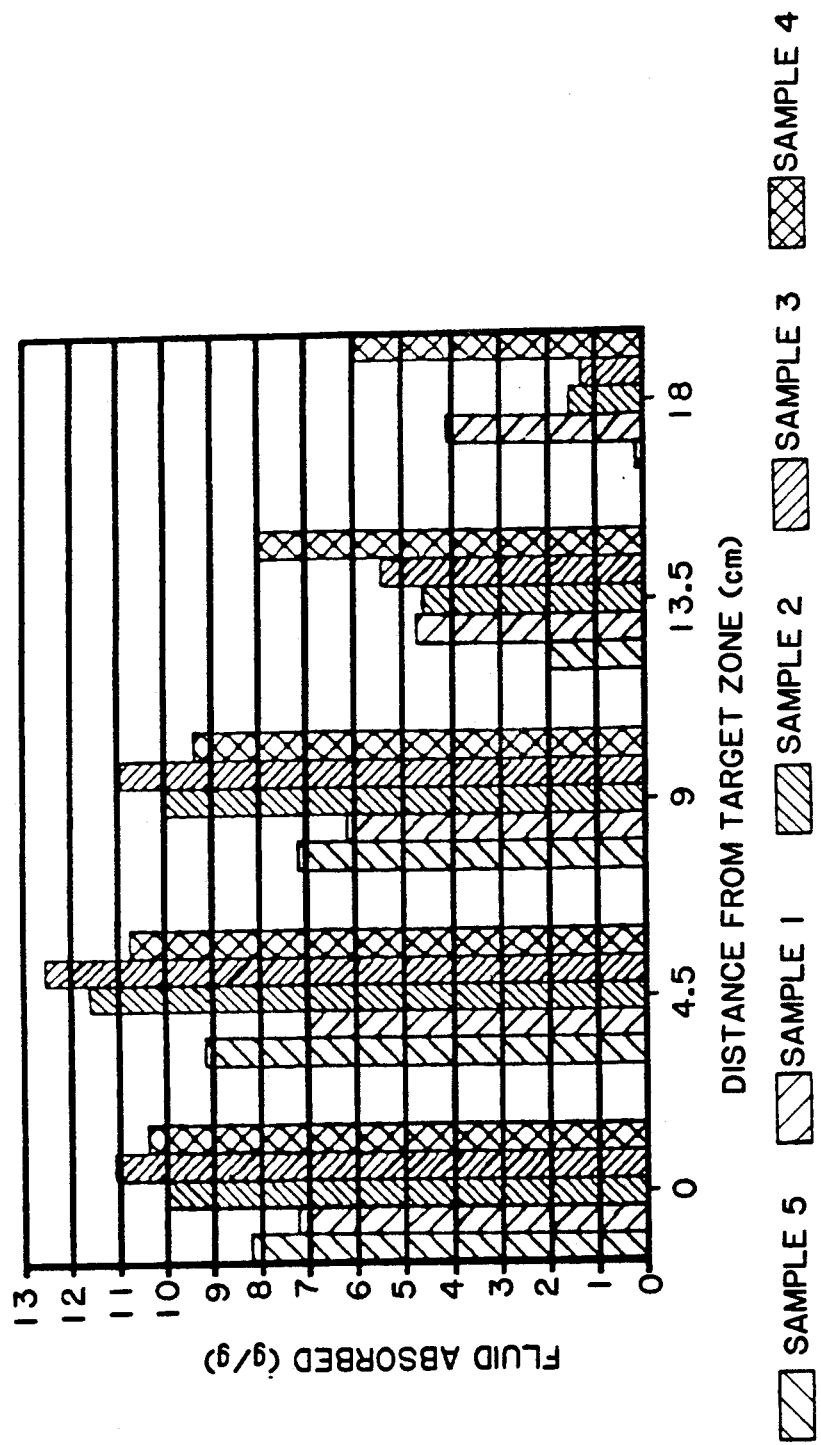
FIG. 6 is a graphical representation of the fluid distribution data set forth in Table 3.

FIG. 6 is a bar graph illustrating the fluid distribution data set forth in Table 3. From FIG. 6 it can be seen that all of the inflated rayon fiber webs possess wicking properties superior to the wood pulp fluff at distances greater than about nine (9) centimeters. At a distance of about eighteen (18) centimeters, it is seen that the oriented carded web possesses an excellent fluid distribution of six (6) grams of fluid per gram of fiber.

EXAMPLE 4

Inflated rayon fibers having a denier of 1.5 and commercially available from Courtaulds, North America, Inc., under the trade designation Courcel TM or Viloft TM are provided in the form of 1-9/16 inch staple. The staple thus provided is formed into a carded web. The carded web is subjected to solvent extraction using methanol as the solvent to remove the surface finish. The process employed is the same set forth in Example 2. The web is then subjected to a wet crosslinking process employing 1,3-dichloro-2-propanol as the crosslinking agent. The crosslinking process is performed in the following manner.

A crosslinking solution is prepared by dissolving 50 grams of sodium chloride in 400 milliliters of distilled water. Fifty grams (50g) of sodium hydroxide is then added to the sodium chloride solution along with an additional 400 milliliters of distilled water. One hundred grams (100 g) of 1,3-dichloro-2-propanol is then added to the solution. Distilled water is added to bring the total volume of crosslinking solution up to one liter.

One hundred grams (100 g) of the fiber web is placed in an open mesh polypropylene scrim, heat sealed about its perimeter and placed in an open dish reaction vessel. The crosslinking solution is poured over the web into the reaction vessel. The web is kneaded to evenly distribute the crosslinking solution. The reaction vessel is sealed with plastic and allowed to stand at room temperature for 18 hours. The web is then squeezed to remove a portion of the liquid and washed with two liters of distilled water. The washing and squeezing steps are repeated 5 times (6 washes total). The fibers are then air dried at room temperature.

A series of crosslinked webs is prepared. The crosslinked webs are then densified, in a press (Dake), to densities between 0.07 and 0.4 grams per cubic centimeter. The densified webs thus formed are then tested to determine their vertical wicking properties. The results of the vertical wicking property determinations are set forth in Table 4.

For comparison, carded webs are prepared from inflated rayon fibers as set forth above except the webs are not subjected to a crosslinking process. The webs are densified in a press (Dake) to densities between 0.10 and 0.3 grams per cubic centimeter. These webs are similarly subjected to a vertical wicking property determination. The results are similarly set forth in Table 4.

TABLE 4

| Web Density q/cc | Vertical Wicking Rate | | | | | | Vertical Wicking Capacity | | Fluid Distribution (q/q) | | | | |
|---|---|---|---|---|---|---|---|---|---|---|---|---|---|
| | Initial | 10 Sec[1] | 15 Sec[1] | 20 Sec[1] | 25 Sec[1] | 30 Sec[1] | 15 Min | 30 Min | 0[1] | 4.5 | 9 | 13.5 | 18 |
| Crosslinked | | | | | | | | | | | | | |
| 0.07 | 86.8 | 41.1 | 21.4 | 4.6 | 1.3 | 0.7 | 894 | 899 | 11.5 | 11.1 | 10.8 | 10.2 | 8.9 |
| 0.10 | 80.6 | 40.0 | 26.8 | 4.7 | — | — | 880 | 890 | 10.7 | 10.7 | 10.5 | 10.0 | 8.7 |
| 0.15 | 78.1 | 42.8 | 27.1 | 2.9 | — | — | 859 | 867 | 10.5 | 10.0 | 10.2 | 9.7 | 8.6 |
| 0.18 | 74.7 | 45.4 | 30.0 | — | — | — | 868 | 878 | 10.6 | 10.4 | 10.5 | 10.0 | 8.9 |
| 0.30 | 78.7 | 47.3 | 27.8 | 3.7 | — | — | 900 | 910 | 10.9 | 11.3 | 11.1 | 10.5 | 9.2 |
| 0.40 | 76.1 | 47.4 | 27.6 | — | — | — | 881 | 889 | 10.5 | 10.8 | 10.7 | 10.0 | 8.8 |
| Non-crosslinked | | | | | | | | | | | | | |
| 0.10 | 72.0 | — | — | — | — | — | 616 | 650 | 11.3 | 12.2 | 11.0 | 4.2 | 1.0 |
| 0.15 | 64.0 | — | — | — | — | — | 713 | 748 | 9.9 | 11.4 | 10.0 | 8.4 | 5.5 |
| 0.30 | 60.0 | — | — | — | — | — | 717 | 742 | 9.1 | 10.6 | 9.5 | 7.6 | 5.5 |

— Not measured
[1]Height in centimeters

Figure 7:
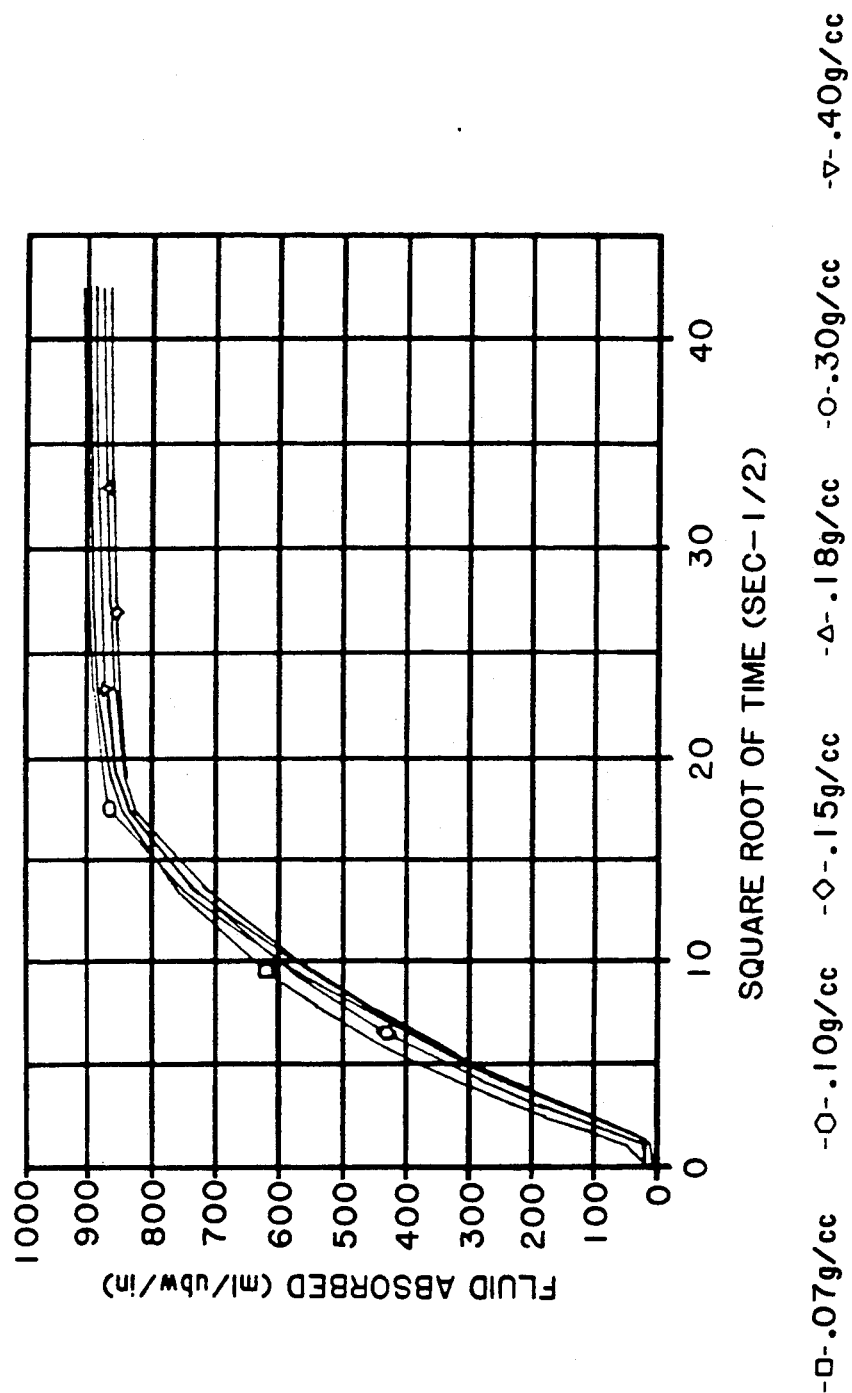
FIG. 7 is a graphical representation of the vertical wicking data set forth in Table 4 for the crosslinked samples.
Figure 8:
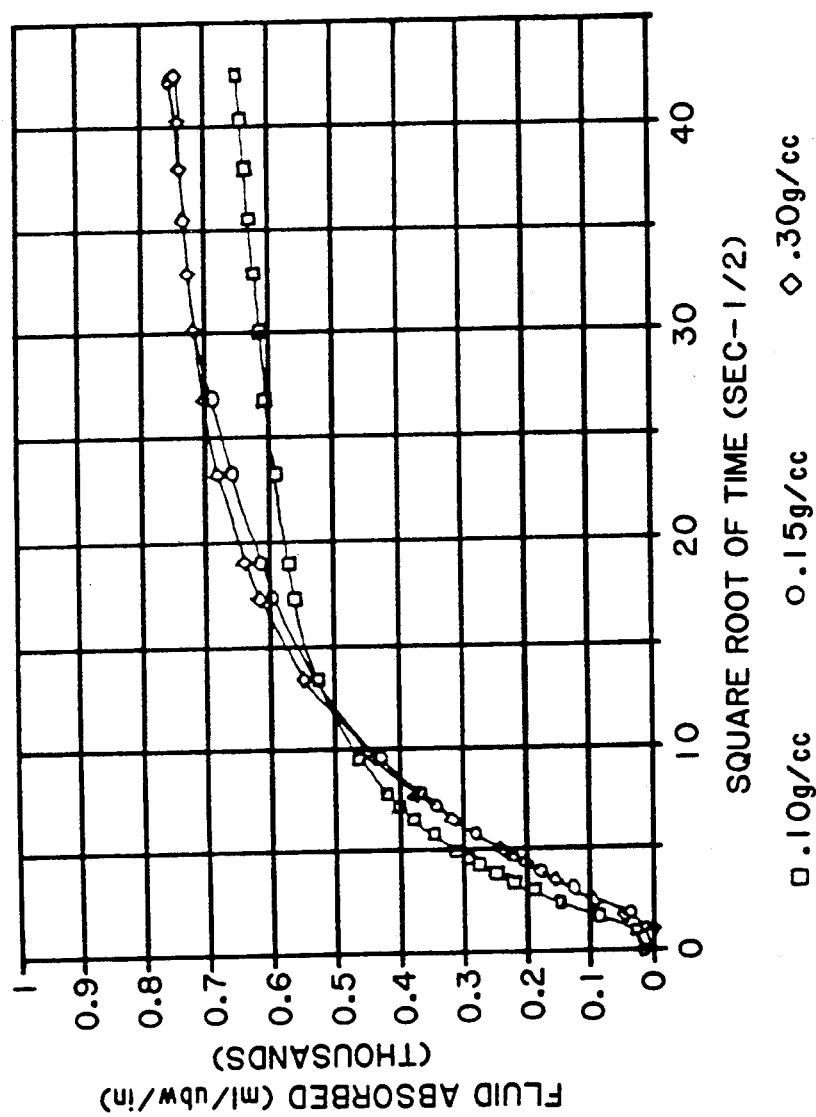
FIG. 8 is a graphical representation of the vertical wicking data for the materials in Table 4 for the non-crosslinked samples.

FIG. 7 graphically illustrates the vertical wicking test data set forth in Table 4 for the crosslinked samples. As can be seen from FIG. 7, density does not have a significant effect on the vertical wicking rates of the carded crosslinked webs. FIG. 8 graphically illustrates the vertical wicking test data set forth in Table 4 for the non-crosslinked samples. It is seen from FIGS. 7 and 8 that crosslinking of the carded webs significantly improves the vertical wicking rate when compared to a non-crosslinked web.

Figure 9:
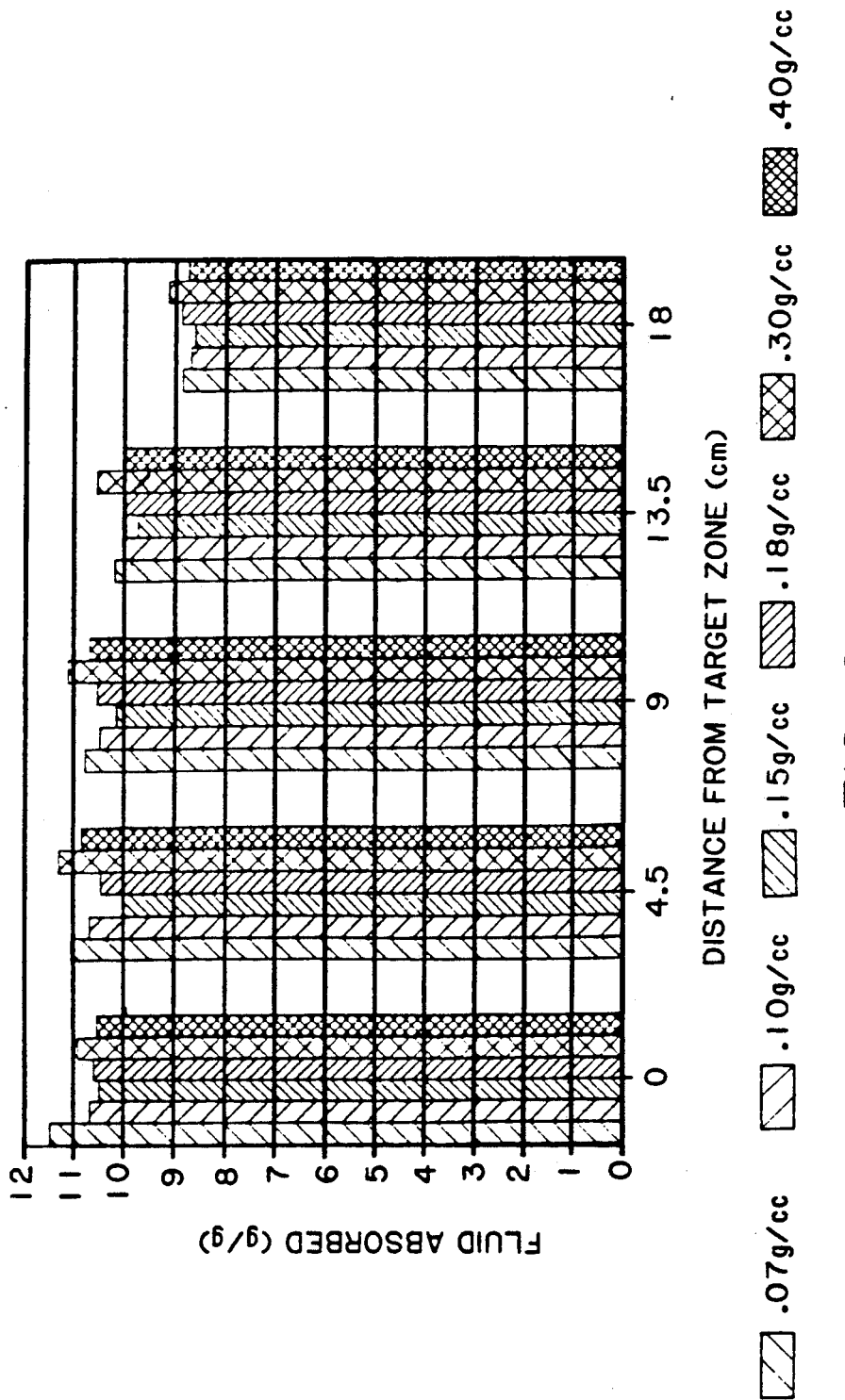
FIG. 9 is a graphical representation of the fluid distribution data for the materials in Table 4 for the crosslinked samples.
Figure 10:
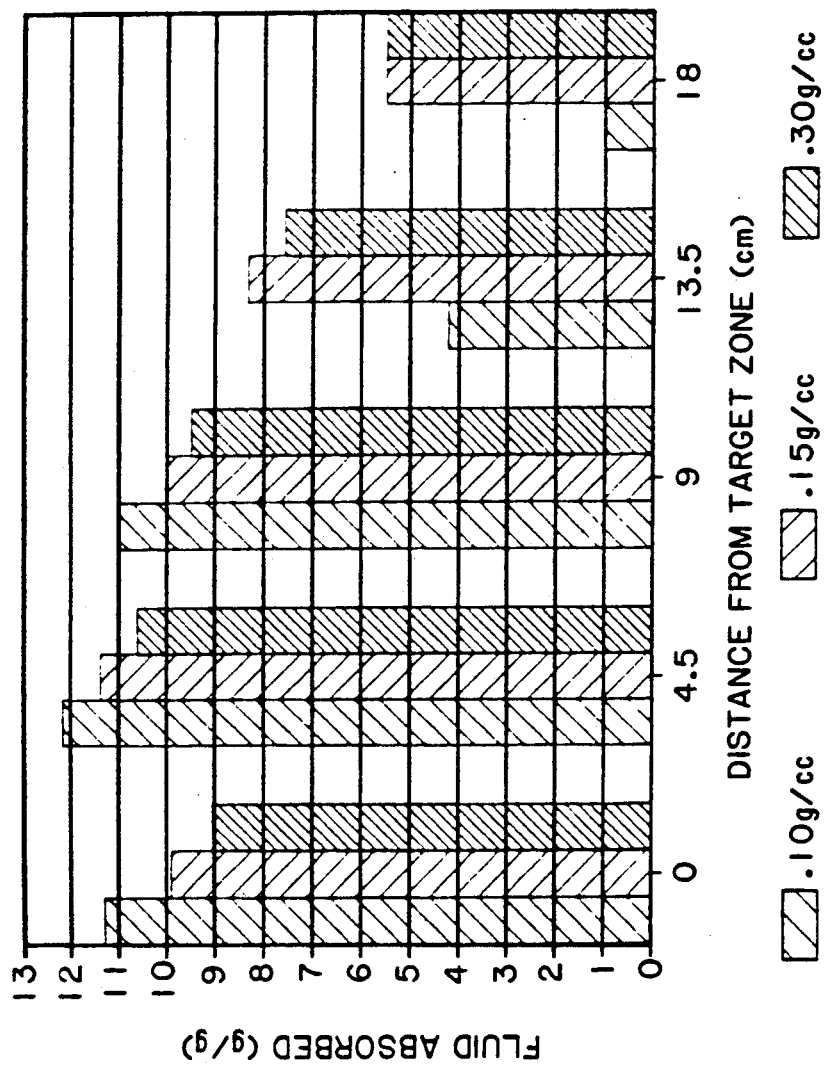
FIG. 10 is a graphical representation of the fluid distribution data set forth in Table 4 for the non-crosslinked samples.

FIG. 9 is a bar graph illustrating the fluid distribution data set forth in Table 4 for the crosslinked samples. As can be seen from reference to FIG. 9, the fluid distribution properties of all the crosslinked webs are excellent and roughly equivalent. FIG. 10 is a bar graph illustrating the fluid distribution data set forth in Table 4 for the non-crosslinked samples. It is seen from FIGS. 9 and 10 that the crosslinked webs possess better fluid distribution properties at distances generally greater than nine (9) centimeters when compared to the non-crosslinked web of inflated rayon fibers.

EXAMPLE 5

A super inflated rayon fiber commercially available from Courtaulds North America, under the trade designation SI TM rayon is provided. The super inflated fiber is in the form 1-9/16 inch staple and has a denier of about 3 and differs from the inflated rayon fibers previously employed in that it is believed to be somewhat more inflated than the Courcel previously employed in Example 4 [see, *Journal of Industrial Fabrics.* Vol.4, No.1:4–17, (1985)]. The super inflated rayon fiber is formed into a carded web and is subjected to solvent extraction employing methanol as a solvent through a Soxhlet extraction process, as described in Example 2. Two such webs are formed. One of the webs is subjected to a crosslinking process employing 1,3-dichloro-2-propanol as a crosslinking agent in the process set forth in connection with Example 4. The other web is not subjected to a crosslinking process. Both webs are then densified in a press (Dake) to a density of about 0.15 grams per cubic centimeter.

Figure 13:
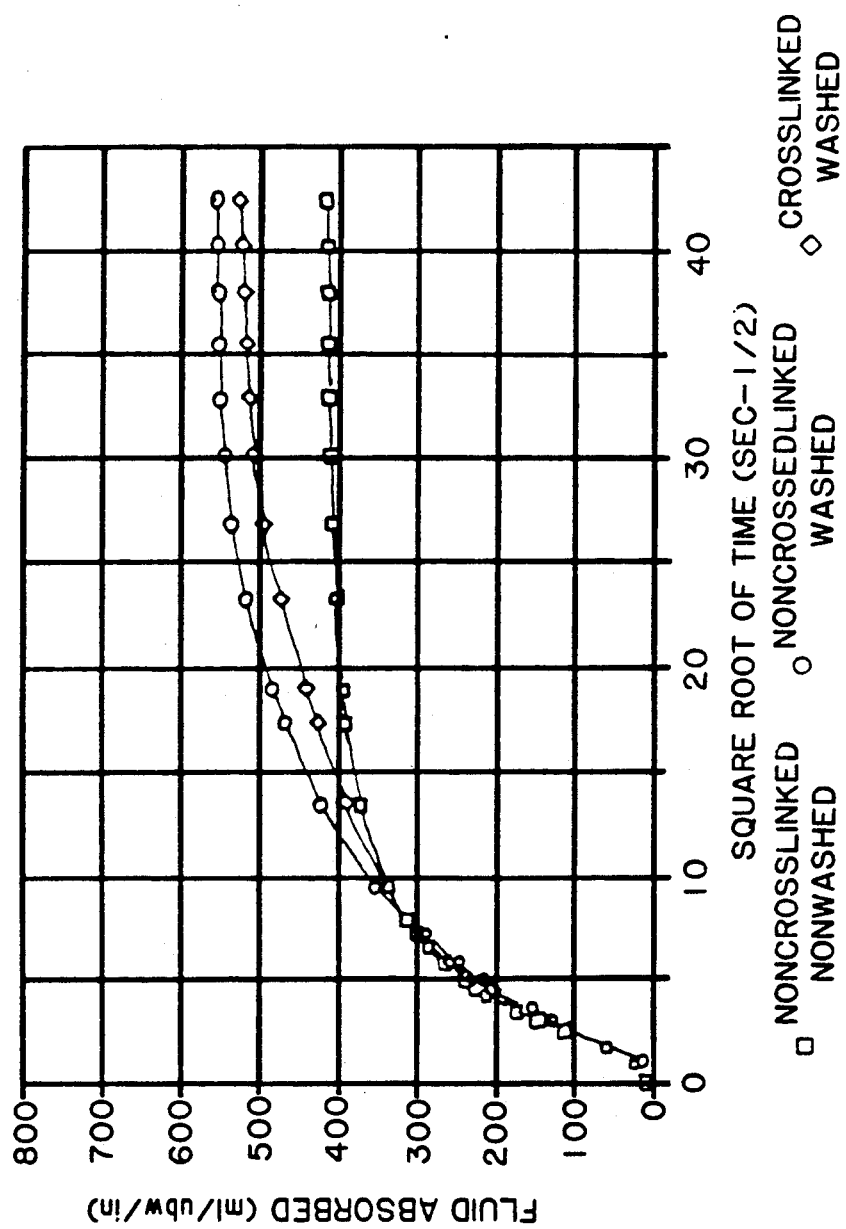
FIG. 13 is a graphical representation of the vertical wicking data for the materials in Table 6.

The vertical wicking properties of both webs are then determined. The results of these determinations are set forth in Table 5.

from reference to FIG. 13, the crosslinked washed and non-crosslinked washed webs formed from solid core rayon fibers exhibit similar vertical wicking rates.

Figure 14:
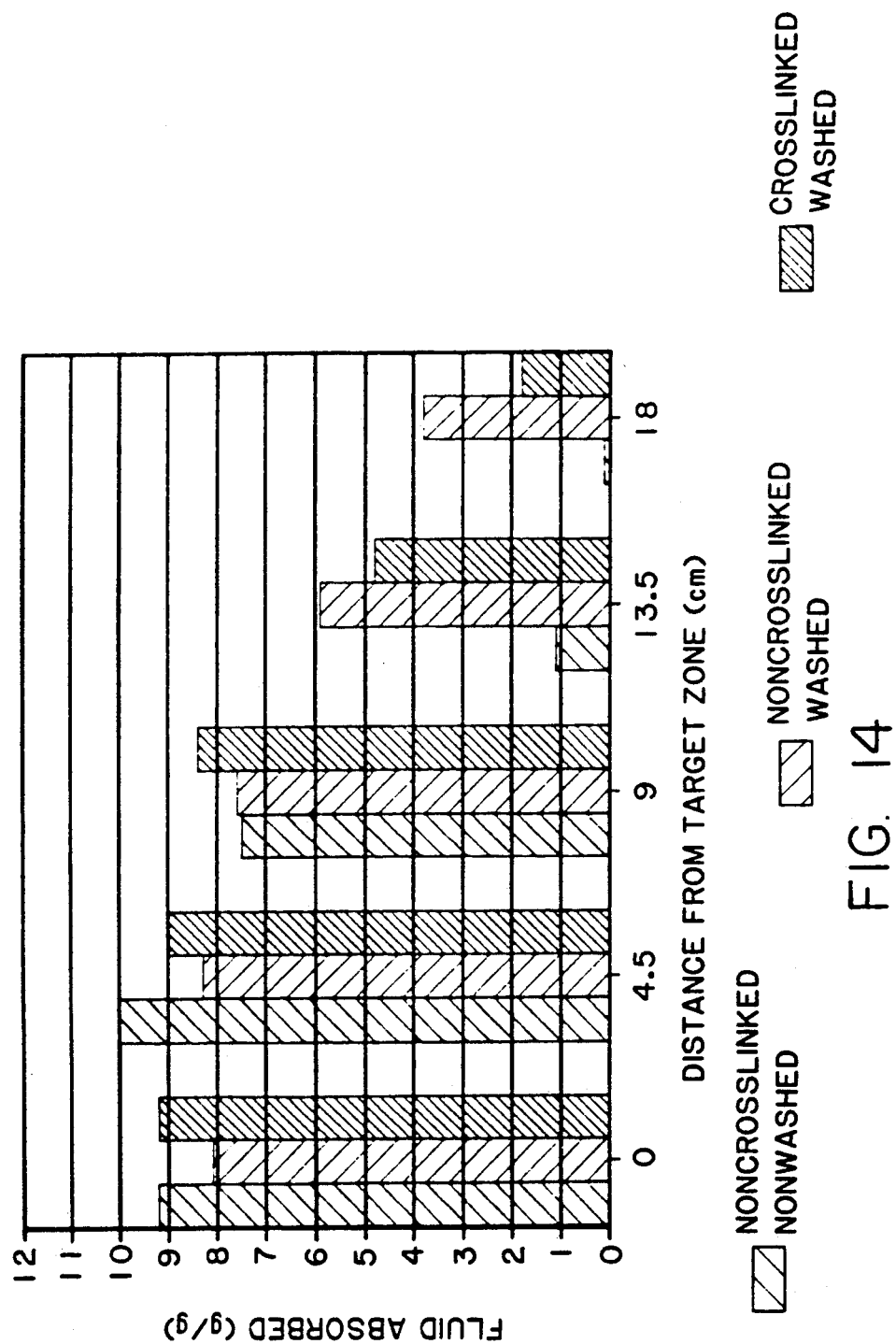
FIG. 14 is a graphical representation of the fluid distribution data set forth in Table 6.

FIG. 14 is a bar graph illustrating the fluid distribution data set forth in Table 6. As can be seen from reference to FIG. 14, the crosslinked washed web possesses somewhat better fluid distribution properties up to a distance of about nine (9) centimeters. For distances greater than about nine centimeters, the non-crosslinked washed web exhibits superior fluid distribution properties.

TABLE 5

| Web Density q/cc | Vertical Wicking Rate | | | | | | Vertical Wicking Capacity | | Fluid Distribution (q/q) | | | | |
|---|---|---|---|---|---|---|---|---|---|---|---|---|---|
| | Initial | 10 Sec[1] | 15 Sec[1] | 20 Sec[1] | 25 Sec[1] | 30 Sec[1] | 15 Min | 30 Min | 0[1] | 4.5 | 9 | 13.5 | 18 |
| Crosslinked | | | | | | | | | | | | | |
| 0.15 | 92.5 | 35.4 | 17.4 | 10.5 | 6.8 | 3.9 | 945 | 972 | 15.0 | 15.2 | 14.2 | 10.8 | 6.5 |
| Non-crosslinked | | | | | | | | | | | | | |
| 0.15 | 63.6 | 30.6 | 17.5 | 10.9 | 8.2 | 5.3 | 761 | 802 | 10.8 | 12.4 | 11.4 | 8.1 | 4.6 |

[1]Height in centimeters

Figure 11:
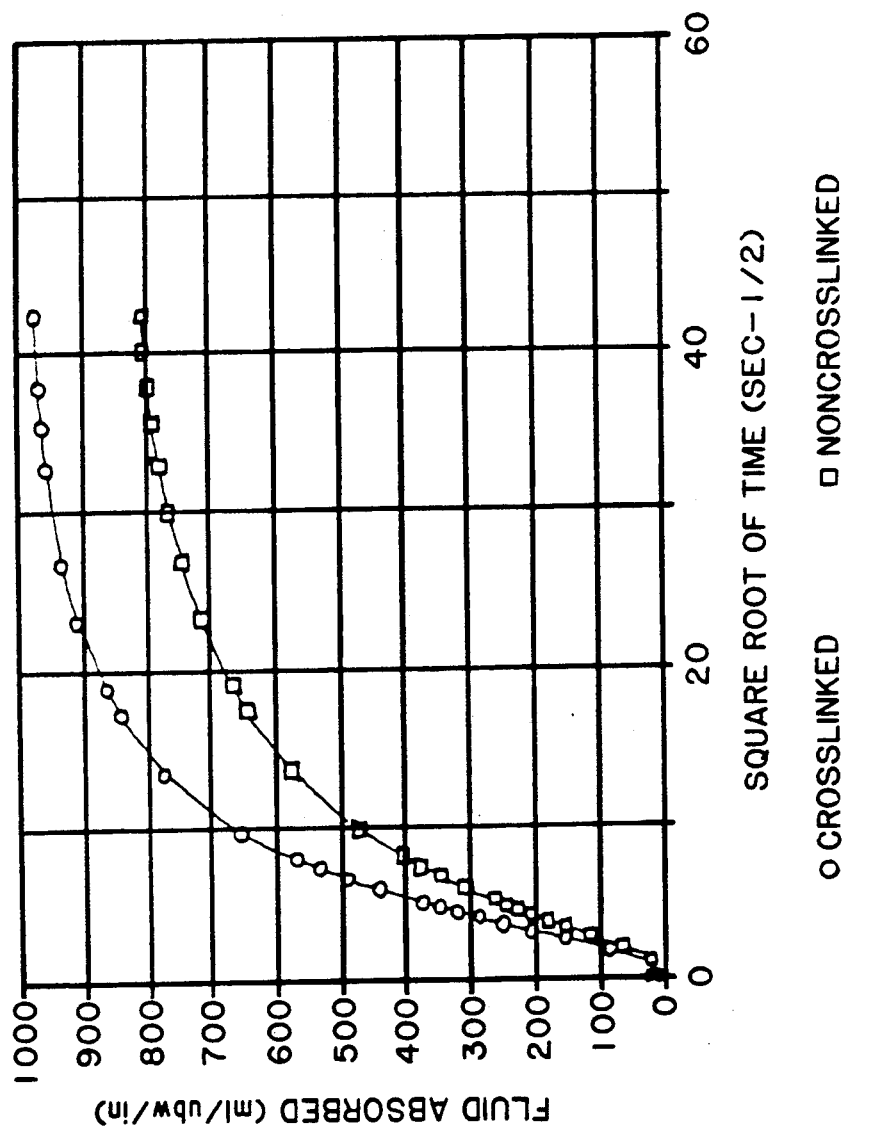
FIG. 11 is a graphical representation of the vertical wicking data set forth in Table 5.

FIG. 11 graphically illustrates the vertical wicking rates set forth in Table 5. As can be seen from reference to FIG. 11, the crosslinked web of super inflated rayon fibers possesses a significantly greater vertical wicking rate than the non-crosslinked web.

Figure 12:
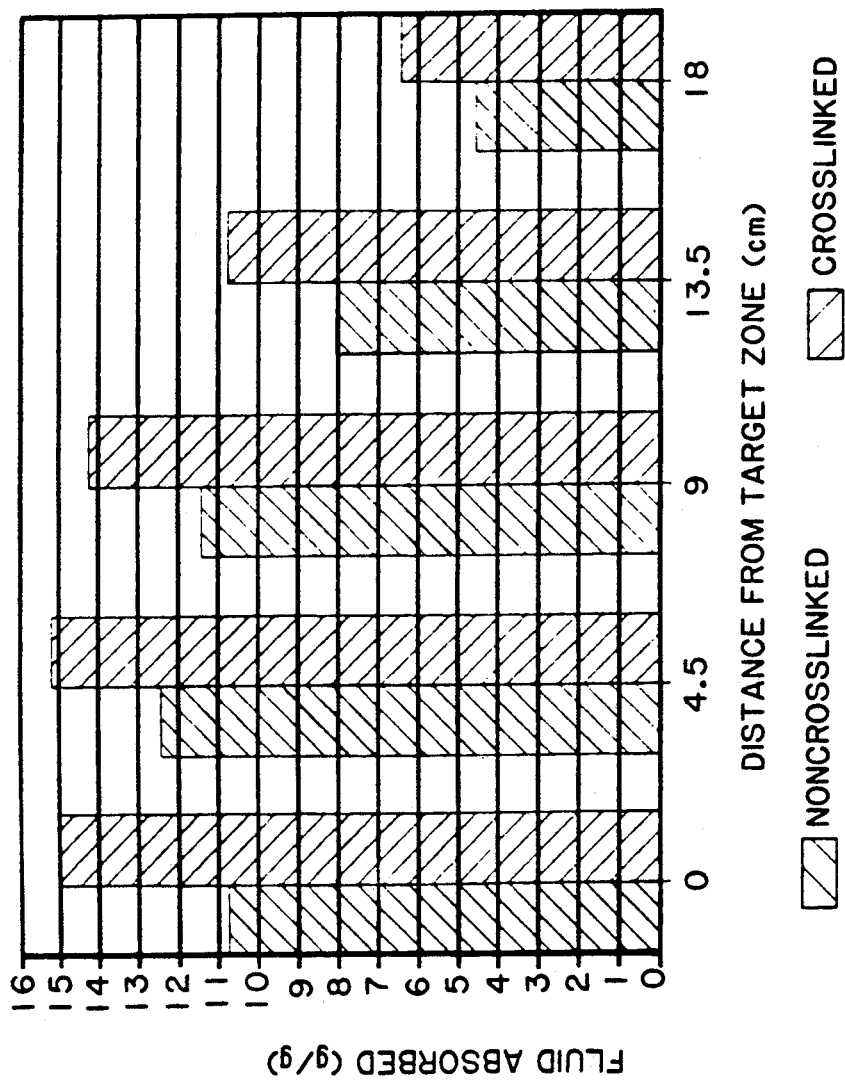
FIG. 12 is a graphical representation of the fluid distribution data set forth in Table 5.

FIG. 12 is a bar graph illustrating the fluid distribution data set forth in Table 5. As can be seen from reference to FIG. 12, the crosslinked web of super inflated rayon fibers possesses improved fluid distribution properties at all distances tested.

EXAMPLE 6

Solid core crimped rayon fibers commercially available from Courtaulds, North America, Inc. under the trade designation Sarille TM are provided. The fibers have a denier of about 2.2 and are in the form of 1.25 inch staple. The staple is then formed into carded webs. Three webs are formed. One of the webs is subjected to a crosslinking process employing 1,3-dichloro-2-propanol as the crosslinking agent in the process set forth in Example 4. The other two webs are not subjected to a crosslinking process. The crosslinked web and one of the non-crosslinked webs are then subjected to 6 washings with distilled water to remove the glycerin finish. The webs are then densified in a press (Dake) to a density of about 0.15 grams per cubic centimeter.

The vertical wicking properties of the webs are then determined. The results of this determination are set forth in Table 6.

TABLE 6

| Web Density q/cc | Vertical Wicking rate, Initial | Vertical Wicking Capacity | | Fluid Distribution (q/q) | | | | |
|---|---|---|---|---|---|---|---|---|
| | | 15 Min | 30 Min | 0[1] | 4.5 | 9 | 13.5 | 18 |
| Non-crosslinked washed | | | | | | | | |
| 0.15 | 52.6 | 546 | 557 | 8.1 | 8.3 | 7.6 | 5.9 | 3.8 |
| Crosslinked washed | | | | | | | | |
| 0.15 | 56.6 | 509 | 527 | 9.2 | 9.0 | 8.4 | 4.8 | 1.8 |
| Non-crosslinked non-washed | | | | | | | | |
| 0.15* | 57.3 | 410 | 417 | 9.2 | 10.0 | 7.5 | 1.1 | 0.1 |

*Not an example of the present invention
[1]Height in centimeters

FIG. 13 graphically illustrates the vertical wicking properties for the materials in Table 6. As can be seen Comparison of FIGS. 7, 8 and 13 reveals that crosslinking improves the vertical wicking rates of inflated rayon fibers but lowers, albeit slightly, the vertical wicking rates of solid core rayon fibers. Additionally, comparison of FIGS. 9, 10 and 14 demonstrates that the fluid distribution properties for crosslinked and non-crosslinked inflated rayon fiber webs differ to a greater extent than the fluid distribution properties for crosslinked washed and non-crosslinked washed solid core rayon fiber webs.

Thus, it is seen that crosslinking has little effect on solid core rayon fiber webs and in fact appears to deleteriously affect certain properties. However, crosslinking significantly improves the vertical wicking rate, vertical wicking capacity and fluid distribution properties of inflated rayon fibers.

EXAMPLE 7

Inflated scoured rayon fiber tow having a denier of 1.5 and commercially available from Courtaulds North America, under the trade designation Courcel TM is provided in 16 inch lengths. Forty-five grams of the fiber is provided and combed to separate the fiber filaments. The combed fibers are placed in a glass dish. To the glass dish is added 500 milliliters of a crosslinking solution comprising, by volume, 20 percent formalin, 50 percent hydrochloric acid (37%) and 30 percent distilled water. The crosslinking solution is allowed to remain in contact with the rayon fiber present in the glass dish for 30 minutes at room temperature.

The rayon fiber is removed from the glass dish, washed with distilled water, neutralized with a 5% aqueous sodium carbonate solution, washed three more times with distilled water and air dried. The fibers are then subjected to soxhlet extraction using methanol as the solvent. After evaporation of the methanol solvent, the tow is again combed to separate the filaments. Ten 15×3 inch segments are prepared for vertical wicking property characterization. Each sample is densified to about 0.15 grams per cubic centimeter and weighs 4.5 grams.

Control samples of non-crosslinked inflated rayon fibers are similarly prepared except the fibers are not exposed to the formalin containing crosslinking solution. Otherwise, the control samples are prepared as set forth above.

The test samples are then subjected to vertical wicking property determinations. The results of this determination are set forth in Table 7.

TABLE 7

| Density (g/cc) | Vertical Wicking Rate, Initial | Vertical Wicking Capacity, 15 min. | Fluid Distribution (q/q) | | | | |
|---|---|---|---|---|---|---|---|
| | | | $0^1$ | 4.5 | 9 | 13.5 | 18 |
| | | Crosslinked | | | | | |
| 0.14 | 22.4 | 667 | 9.9 | 10.0 | 8.8 | 6.7 | 5.4 |
| | | Non-crosslinked | | | | | |
| 0.13 | 39.0 | 518 | 7.3 | 6.7 | 5.5 | 4.7 | 4.0 |

[1] Height in centimeters

Figure 15:
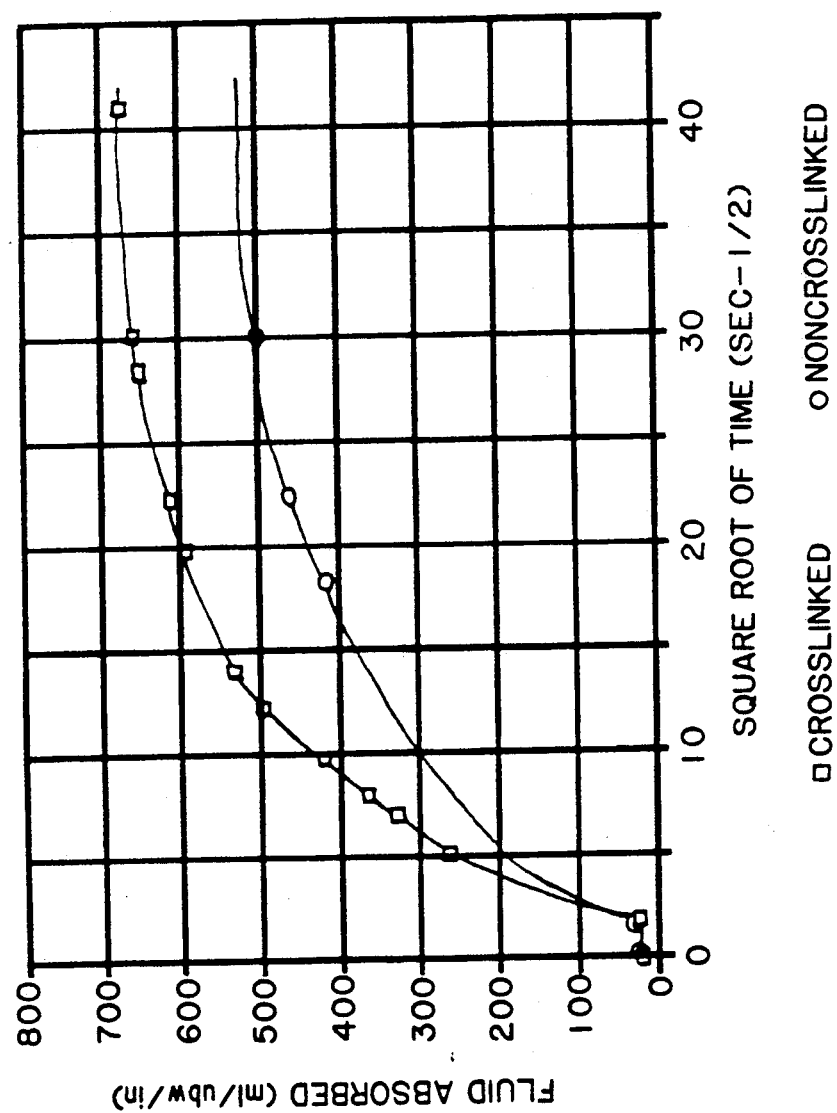
FIG. 15 is a graphical representation of the vertical wicking data for the materials in Table 7.

FIG. 15 is a graphical representation of the vertical wicking rates of the test samples of Example 7. As can be seen from reference to FIG. 15, the crosslinked materials according to the present invention have significantly improved vertical wicking rates compared to the non-crosslinked control samples.

Figure 16:
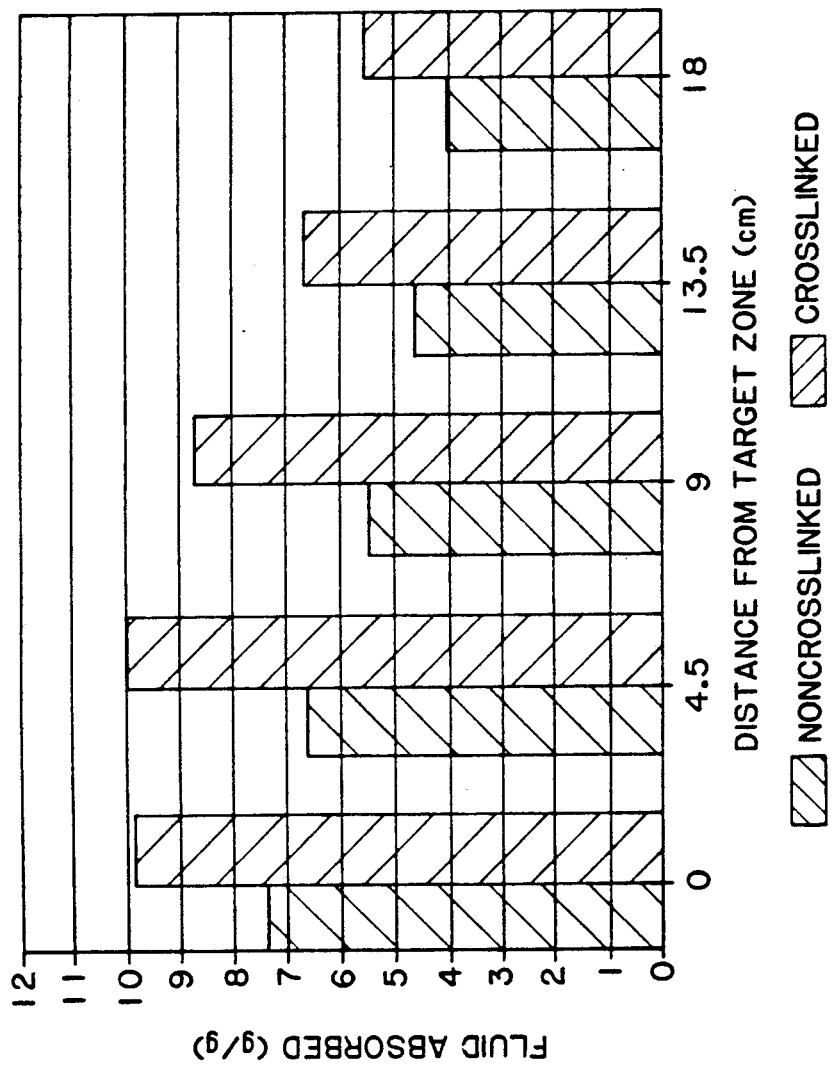
FIG. 16 is a graphical representation of the fluid distribution data set forth in Table 7.

FIG. 16 is a bar graph representing the fluid distribution data set forth in Table 7. Again, FIG. 16 demonstrates the improved vertical wicking properties of the crosslinked material according to the present invention compared to the non-crosslinked control sample.

As is apparent from the foregoing specification, the present invention is susceptible of being embodied with various alterations and modifications which may differ particularly from those that have been described in the preceding specification and description. For this reason, it is to be understood that all of the foregoing is intended to be merely illustrative and is not to be construed or interpreted as being restrictive or otherwise limiting of the present invention, excepting as it is set forth and defined in the following claims.

What is claimed:

1. An absorbent web of a material, said material comprising inflated cellulose fibers, said fibers being formed from regenerated cellulose and being free of a surface finish, said web having a density within the range of from about 0.05 to about 0.4 grams per cubic centimeter, possessing improved vertical wicking properties compared to a similar web of inflated, regenerated cellulose fibers which comprise a surface finish.

2. The absorbent web of claim 1 wherein said inflated cellulose fibers are at least partially collapsed.

3. The absorbent web according to claim 1 wherein at least one of the initial vertical wicking rate, vertical fluid capacity at 15 or 30 minutes, or vertical fluid distribution at eighteen (18) centimeters of the said web is at least about 20 percent greater than the corresponding vertical wicking property of said similar web.

4. The absorbent web according to claim 3 wherein at least one of said initial vertical wicking rate, vertical fluid capacity at 15 or 30 minutes, or vertical fluid distribution at eighteen (18) centimeters of said web is at least about 40 percent greater than said corresponding vertical wicking property of said similar web.

5. The absorbent web according to claim 1 wherein at least two of the initial vertical wicking rate, vertical fluid capacity at 15 or 30 minutes, or fluid distribution at a distance of eighteen (18) centimeters are at least about 20 percent greater than the corresponding vertical wicking properties of said similar web.

6. The absorbent web according to claim 5 wherein at least two of said initial vertical wicking rate, vertical fluid capacity at 15 or 30 minutes or vertical fluid distribution at eighteen (18) centimeters are at least about 40 percent greater than the corresponding vertical wicking properties of said similar web.

7. The absorbent web according to claim 3 wherein the inflated cellulose fibers are crosslinked.

8. The web according to claim 7 wherein the inflated cellulose fibers are crosslinked while in a swollen state.

9. The web according to claim 8 wherein the fibers are at least partially collapsed.

10. An absorbent web of a material, said material comprising crosslinked inflated cellulose fibers, said web possessing improved vertical wicking properties when compared to a similar web formed from non-crosslinked inflated cellulose fibers.

11. The absorbent web according to claim 10 wherein the inflated cellulose fibers are formed from regenerated cellulose.

12. The absorbent web according to claim 11 wherein at least one of the initial vertical wicking rate, vertical fluid capacity at 15 or 30 minutes or vertical fluid distribution at eighteen (18) centimeters is at least about 20 percent greater than the corresponding vertical wicking properties of said similar web.

13. The absorbent web according to claim 11 wherein at least one of said initial vertical wicking rate, vertical fluid capacity at 15 or 30 minutes or vertical fluid distribution at eighteen (18) centimeters is at least about 40 percent greater than said corresponding vertical wicking property of said similar web.

14. The absorbent web according to claim 11 wherein at least two of said initial vertical wicking rate, vertical fluid capacity at 15 or 30 minutes or vertical fluid distribution at eighteen (18) centimeters are at least about 20 percent greater than said corresponding vertical wicking properties of said similar web.

15. The absorbent web according to claim 14 wherein at least two of the initial vertical wicking rate, vertical fluid capacity at 15 or 30 minutes or vertical fluid distribution at eighteen (18) centimeters is at least about 40 percent greater than said corresponding vertical wicking properties of said similar web.

16. The absorbent web according to claim 12, wherein the inflated cellulose fiber is at least partially collapsed.

17. An absorbent product, said product comprising a web of an absorbent material, said web comprising inflated cellulose fibers, said fibers being formed from regenerated cellulose and being free of a surface finish, said web possessing improved vertical wicking properties when compared to a similar web formed from inflated, regenerated cellulose fibers which comprise a surface finish.

18. The absorbent product according to claim 17 wherein said absorbent product is a diaper further comprising an outer water-impervious layer adjacent said absorbent web of inflated cellulose fibers, and a water-pervious liner layer adapted to contact the skin of the wearer and adjacent to said absorbent web.

19. The diaper according to claim 18 wherein said diaper further comprises an amount of a water-swellable polymeric material in flow communication with said absorbent web.

20. The diaper according to claim 19 wherein said water-swellable polymeric material is present within said absorbent web.

21. The diaper according to claim 20 wherein said absorbent web transports a liquid applied to said absorbent web at a first location to said water-swellable polymer present at a second location in said absorbent web.

22. The diaper according to claim 21 wherein said inflated cellulose fiber is at least partially collapsed.

23. The diaper according to claim 21 wherein said inflated cellulose fibers are crosslinked.

24. An absorbent product, said product comprising a web of an absorbent material, said web comprising crosslinked inflated cellulose fibers, said web possessing improved vertical wicking properties when compared to a similar web formed from non-crosslinked inflated cellulose fibers.

25. The absorbent product according to claim 24 wherein said absorbent product is a diaper further comprising an outer water-impervious layer adjacent said absorbent web of inflated cellulose fibers, and a water-pervious liner layer adapted to contact the skin of a wearer and adjacent said absorbent web.

26. The diaper according to claim 25 wherein said diaper further comprises an amount of a water-swellable polymeric material in flow communication with said absorbent web.

27. The diaper according to claim 26 wherein said water-swellable polymeric material is present within said absorbent web.

28. The diaper according to claim 27 wherein said absorbent web transports a liquid applied to said absorbent web at a first location to said water-swellable polymer present at a second location in said absorbent web.

29. The diaper according to claim 28 wherein said inflated cellulose fiber is at least partially collapsed.

30. The diaper according to claim 29 wherein said inflated cellulose fibers are free of a surface finish.

31. The absorbent web according to claim 1 wherein the web has a density within the range of from about 0.1 to about 0.2 grams per cubic centimeter.

32. The absorbent web according to claim 7 wherein the web has a density within the range of from about 0.07 to about 0.2 grams per cubic centimeter.

* * * * *

UNITED STATES PATENT AND TRADEMARK OFFICE
CERTIFICATE OF CORRECTION

PATENT NO. : 5,124,197
DATED : June 23, 1992
INVENTOR(S) : Leo J. Bernardin; Patti J. Rhode; Catherine J. Heimbach It is certified that error appears in the above-identified patent and that said Letters Patent is hereby corrected as shown below:

Column 8, Line 21, delete the raised number "$\frac{1}{78}$" and substitute therefor --$\frac{1}{2}$--.

Column 12, TABLE 3, under the column, <u>Vertical Wicking Rate, Initial</u>, delete the number "21" and substitute therefor --31--.

Signed and Sealed this

Fourteenth Day of December, 1993

Attest:

BRUCE LEHMAN

*Attesting Officer*     Commissioner of Patents and Trademarks